(12) United States Patent
Boronyak et al.

(10) Patent No.: US 8,852,923 B2
(45) Date of Patent: Oct. 7, 2014

(54) FLOW-STRETCH-FLEXURE BIOREACTOR

(75) Inventors: Steven M. Boronyak, Kingwood, TX (US); George C. Engelmayr, Jr., Cambridge, MA (US); Sharan Ramaswamy, Miami, FL (US); Michael S. Sacks, Pittsburgh, PA (US); David E. Schmidt, Pittsburgh, PA (US); Mohammed S. El-Kurdi, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 600 days.

(21) Appl. No.: 12/959,906

(22) Filed: Dec. 3, 2010

(65) Prior Publication Data

US 2011/0212500 A1 Sep. 1, 2011

Related U.S. Application Data

(60) Provisional application No. 61/266,231, filed on Dec. 3, 2009.

(51) Int. Cl.
C12M 3/00 (2006.01)
C12M 1/24 (2006.01)
C12M 1/42 (2006.01)

(52) U.S. Cl.
CPC .............. *C12M 21/08* (2013.01); *C12M 23/08* (2013.01); *C12M 35/04* (2013.01)
USPC ....................................... 435/289.1; 435/174

(58) Field of Classification Search
CPC ....... C12M 21/08; C12M 23/08; C12M 35/04
USPC ............ 435/174, 284.1, 286.5, 298.1–298.2; 600/36, 916, 921
See application file for complete search history.

(56) References Cited

U.S. PATENT DOCUMENTS 6,174,719 B1 * 1/2001 Elizondo et al. ........... 435/284.1
2004/0219659 A1 * 11/2004 Altman et al. ............. 435/284.1
2005/0286103 A1 12/2005 Yu et al.
2006/0223049 A1 * 10/2006 Dancu et al. ................... 435/1.2

OTHER PUBLICATIONS

Engelmayr et al. (Annals of Biomedical Engineering, 36(5), 700-712 (2008)).*
Arnsdorf et al., Non-Canonical Wnt Signaling and N-Cadherin Related alpha-Catenin Signaling Play a Role in Mechanically Induced Osteogenic Cell Fate, PLoS ONE, Apr. 2009, p. e5388, vol. 4, Issue 4.
Arnsdorf et al., Mechanically induced osteogenic differentiation—the role of RhoA, ROCKII and cytoskeletal dynamics, Journal of Cell Science, 2009, pp. 546-553, vol. 122.
Balguid et al., Hypoxia Induces Near-Native Mechanical Properties in Engineered Heart Valve Tissue, Circulation, 2009, pp. 290-297, vol. 119.

(Continued)

*Primary Examiner* — Michael Hobbs
*Assistant Examiner* — Liban Hassan
(74) *Attorney, Agent, or Firm* — The Webb Law Firm

(57) ABSTRACT

Described herein is a bioreactor system and modules capable of developing physiologically relevant fluid-induced shear stresses and regionally specific flow patterns to scaffold specimens and which can couple these stresses to cyclic flexure and/or stretch states. Methods of use of the bioreactor system and module also are provided.

20 Claims, 12 Drawing Sheets

(56) References Cited

OTHER PUBLICATIONS

Bilodeau et al., Design of a Perfusion Bioreactor Specific to the Regeneration of Vascular Tissues Under Mechanical Stresses, Artificial Organs, 2005, pp. 906-922, vol. 29(11).

Cacou et al., A system for monitoring the response of uniaxial strain on cell seeded collagen gels, Medical Engineering & Physics, 2000, pp. 327-333, vol. 22.

Doty et al., Magnetism in High-Resolution NMR Probe Design. I: General Methods, Concepts Magn Reson, 1998, pp. 133-156, vol. 10.

Dumont et al., Design of a New Pulsatile Bioreactor for Tissue Engineered Aortic Heart Valve Formation, Artif Organs, 2002, pp. 710-714, vol. 26, No. 8.

Engelmayr Jr. et al., A novel bioreactor for the dynamic flexural stimulation of tissue engineered heart valve biomaterials, Biomaterials, 2003, pp. 2523-2532, vol. 24.

Engelmayr Jr. et al., The independent role of cyclic flexure in the early in vitro development of an engineered heart valve tissue, Biomaterials, 2005, pp. 175-187, vol. 26.

Engelmayr Jr. et al., Cyclic flexure and laminar flow synergistically accelerate mesenchymal stem cell-mediated engineered tissue formation: Implications for engineered heart valve tissues, Biomaterials, 2006, pp. 6083-6095, vol. 27.

Engelmayr Jr. et al., A Novel Flex-Stretch-Flow Bioreactor for the Study of Engineered Heart Valve Tissue Mechanobiology, Annals of Biomedical Engineering, 2008, pp. 700-712, vol. 36(5).

Flanagan et al., A collagen-glycosaminoglycan co-culture model for heart valve tissue engineering applications, Biomaterials, 2006, pp. 2233-2246, vol. 27.

Hildebrand et al., Design and Hydrodynamic Evaluation of a Novel Pulsatile Bioreactor for Biologically Active Heart Valves, Annals of Biomedical Engineering, Aug. 2004, pp. 1039-1049, vol. 32, No. 8.

Hildebrand, Design and Evaluation of a Novel Pulsatile Bioreactor for Biologically Active Heart Valves, 2003, University of Pittsburgh, School of Engineering: Master's Thesis.

Hoerstrup et al., Functional Living Trileaflet Heart Valves Grown in Vitro, Circulation, 2000, pp. III-44-III-49, vol. 102.

Hoerstrup et al., Tissue Engineering of Functional Trileaflet Heart Valves From Human Marrow Stromal Cells, Circulation, 2002, pp. I-143-I-150, vol. 106.

Hoerstrup et al., New Pulsatile Bioreactor for in Vitro Formation of Tissue Engineered Heart Valves, Tissue Engineering, 2000, pp. 75-79, vol. 6, No. 1.

Hoerstrup et al., Optimized growth conditions for tissue engineering of human cardiovascular structures, The International Journal of Artificial Organs, 2000, pp. 817-823, vol. 23, No. 12.

Jockenhoevel et al., Cardiovascular Tissue Engineering: A New Laminar Flow Chamber for In Vitro Improvement of Mechanical Tissue Properties, ASAIO Journal, 2002, pp. 8-11, vol. 48.

Kim et al., Scaffolds for Engineering Smooth Muscle under Cyclic Mechanical Strain Conditions, Journal of Biomechanical Engineering, Jun. 2000, pp. 210-215, vol. 122.

Li et al., Effects of dextran on proliferation and osteogenic differentiation of human bone marrow-derived mesenchymal stromal cells, Cytotherapy, 2008, pp. 587-596, vol. 10, No. 6.

Li et al., Oscillatory fluid flow affects human marrow stromal cell proliferation and differentiation, Journal of Orthopaedic Research, 2004, pp. 1283-1289, vol. 22.

Mendelson et al., Heart Valve Tissue Engineering: Concepts, Approaches, Progress, and Challenges, Annals of Biomedical Engineering, Dec. 2006, pp. 1799-1819, vol. 34, No. 12.

Mitchell et al., A Device to Apply User-Specified Strains to Biomaterials in Culture, IEEE Transactions on Biomedical Engineering, Feb. 2001, pp. 268-273, vol. 48, No. 2.

Mol et al., Autologous Human Tissue-Engineered Heart Valves: Prospects for Systemic Application, Circulation, 2006, pp. I-152-I-158, vol. 114.

Mol et al., Tissue Engineering of Human Heart Valve Leaflets: a Novel Bioreactor for a Strain-Based Conditioning Approach, Annals of Biomedical Engineering, Dec. 2005, pp. 1778-1788, vol. 33, No. 12.

Ramaswamy et al., Design of a Novel, MRI-compatible Bioreactor for Longitudinal Monitoring of Mechanically Conditioned Engineered Cardiovascular Constructs, International Society for Magnetic Resonance in Medicine, 17th Scientific Meeting, 2009, p. 4400, Honolulu, HI.

Ramaswamy et al., The role of organ level conditioning on the promotion of engineered heart valve tissue development in-vitro using mesenchymal stem cells, Biomaterials, 2010, pp. 1114-1125, vol. 31.

Ramaswamy et al., Effects on specimen motion on flow induced shear stresses in engineered heart valve tissues, 8th World Biomaterials Congress: Crossing Frontiers in Biomaterials and Regenerative Medicine; May 28-Jun. 1, 2008 Amsterdam, The Netherlands.

Robinson et al., Functional Tissue-Engineered Valves from Cell-Remodeled Fibrin with Commissural Alignment of Cell-Produced Collagen, Tissue Engineering, 2008, pp. 83-95, vol. 14, No. 1.

Sacks et al., Heart valve function: a biomechanical perspective, Phil. Trans. R. Soc. B, 2007, pp. 1369-1391, vol. 362.

Sacks et al., Bioengineering Challenges for Heart Valve Tissue Engineering, Annu. Rev. Biomed. Eng., 2009, pp. 289-313, vol. 11.

Schmidt et al., Tissue engineered heart valves based on human cells, Swiss Med Wkly, 2005, pp. 618-623, vol. 135.

Schmidt et al., In Vitro Heart Valve Tissue Engineering, Methods in Molecular Medicine, 2007, pp. 319-330, vol. 140.

Smith et al., Cyclic Stretch Induces the Expression of Vascular Endothelial Growth Factor in Vascular Smooth Muscle Cells, Endothelium, 2001, pp. 41-48, vol. 8(1).

Sodian et al., Tissue Engineering of Heart Valves: In Vitro Experiences, Ann Thorac Surg, 2000, pp. 140-144, vol. 70.

Stock et al., Cardiovascular Physiology During Fetal Development and Implications for Tissue Engineering, Tissue Engineering, 2001, pp. 1-7, vol. 7, No. 1.

Sucosky et al., Design of an Ex Vivo Culture System to Investigate the Effects of Shear Stress on Cardiovascular Tissue, Journal of Biomechanical Engineering, Jun. 2008, pp. 035001-1-035001-8, vol. 130.

Sutherland et al., From Stem Cells to Viable Autologous Semilunar Heart Valve, Circulation, 2005, pp. 2783-2791, vol. 111.

Syedain et al., Controlled cyclic stretch bioreactor for tissue-engineered heart valves, Biomaterials, 2009, pp. 1-7.

Van Den Broek et al., Medium with blood-analog mechanical properties for cardiovascular tissue culturing, Biorheology, 2008, pp. 651-661, vol. 45.

Vesely, Heart Valve Tissue Engineering, Circ Res., 2005, pp. 743-755, vol. 97.

Weston et al., Estimation of the Shear Stress on the Surface of an Aortic Valve Leaflet, Annals of Biomedical Engineering, 1999, pp. 572-579, vol. 27.

Xing et al., Effects of Constant Static Pressure on the Biological Properties of Porcine Aortic Valve Leaflets, Annals of Biomedical Engineering, Apr. 2004, pp. 555-562, vol. 32, No. 4.

Carson et al. "Histotechnology—A Self Instructional Text", 3rd Edition, 2009, pp. 235-236, American Society for Clinical Pathology, Hong Kong.

* cited by examiner

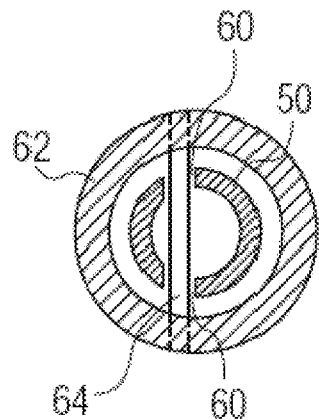
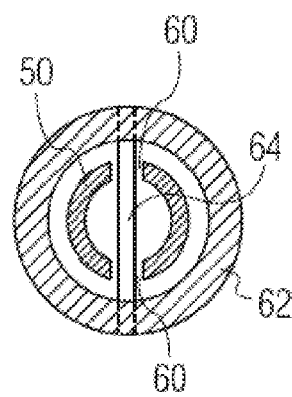
Fig 1E    Fig. 1F
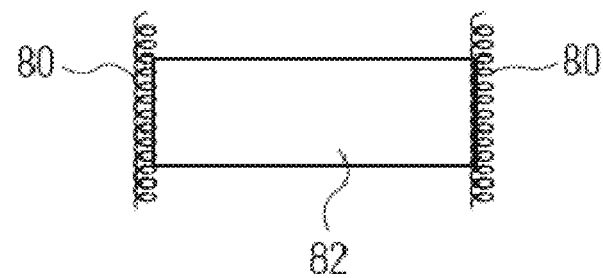
Fig. 1G
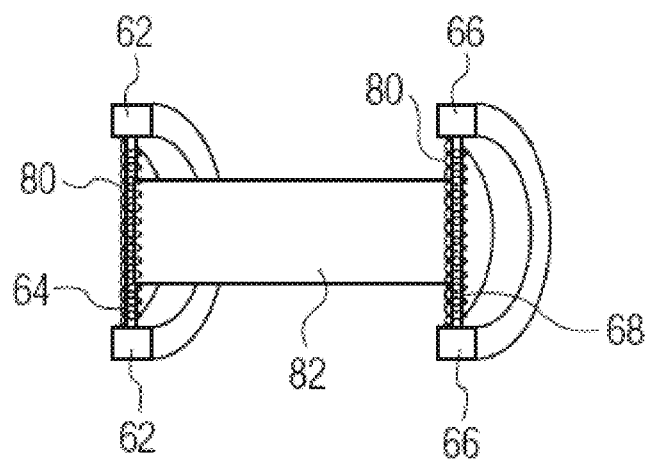
Fig. 1H

Fig. 10

FLOW-STRETCH-FLEXURE BIOREACTOR

CROSS-REFERENCE TO RELATED APPLICATIONS

This application claims the benefit under 35 U.S.C. §119(e) to U.S. Provisional Patent Application No. 61/266,231 filed on Dec. 3, 2009, which is incorporated herein by reference in its entirety.

STATEMENT REGARDING FEDERAL FUNDING

This invention was made with government support under Grant Nos. R01 HL68816 and HL-089750, awarded by the National Institutes of Health. The government has certain rights in the invention.

Tissue engineered heart valves (TEHVs) offer the possibility of accommodating somatic growth, which in principal presents a significant advance over current prosthetic valve replacements for the treatment of congenital heart valve disease (Sacks, M. S., et al. Bioengineering Challenges for Heart Valve Tissue Engineering. Annual Review of Biomedical Engineering, 2009. 11). The need for bioreactors designed for improving the physical integrity of engineered heart valve tissues prior to implantation have been well established (Hoerstrup, S. P., et al. Functional living trileaflet heart valves grown In vitro. Circulation, 2000. 102(19 Suppl 3): p. III44-9; Hoerstrup, S. P., et al. New pulsatile bioreactor for in vitro formation of tissue engineered heart valves. Tissue Eng, 2000. 6(1): p. 75-9; Sodian, R., et al. Tissue engineering of heart valves: in vitro experiences. Ann Thorac Surg, 2000. 70(1): p. 140-4; and Stock, U. A. et al. Vacanti, Cardiovascular physiology during fetal development and implications for tissue engineering. Tissue Eng, 2001. 7(1): p. 1-7). Since then, several studies have shown enhanced cell activity and tissue formation that can occur when simulated physiological culture environments are created in vitro (Xing, Y., Z. et al. Effects of constant static pressure on the biological properties of porcine aortic valve leaflets. Ann Biomed Eng, 2004. 32(4): p. 555-62; Smith, J. D., et al. Cyclic stretch induces the expression of vascular endothelial growth factor in vascular smooth muscle cells. Endothelium, 2001. 8(1): p. 41-8; and Bilodeau, K., et al. Design of a perfusion bioreactor specific to the regeneration of vascular tissues under mechanical stresses. Artif Organs, 2005. 29(11): p. 906-12). At the organ level, several bioreactors that can provide TEHV leaflets with a dynamic conditioning environment that replicates hemodynamic parameters such as arterial pressure and flow conditions have been designed (Hoerstrup, S. P., et al. Optimized growth conditions for tissue engineering of human cardiovascular structures. Int J Artif Organs, 2000. 23(12): p. 817-23; Dumont, K., et al. Design of a new pulsatile bioreactor for tissue engineered aortic heart valve formation. Artif Organs, 2002. 26(8): p. 710-4; and Hildebrand, D. K., et al. Design and hydrodynamic evaluation of a novel pulsatile bioreactor for biologically active heart valves. Ann Biomed Eng, 2004. 32(8): p. 1039-49). Few studies have reported on the usage of these types of devices in actual tissue engineering experiments; rather, most investigations have utilized a simple pulsatile flow loop without consideration to close simulation of pressure and flow magnitudes/waveforms and phase differences between the two. In these studies, improvements such as increased cell viability (Sodian, R., et al. Ann Thorac Surg, 2000. 70(1): p. 140-4) and graded cell/tissue layering with cells orientated with the flow direction (Hoerstrup, S. P., et al. Int J Artif Organs, 2000. 23(12): p. 817-23) were observed.

Recently, we dynamically conditioned TEPVs at normal pulmonary artery pressure conditions and determined that increased collagen formation rates and enhanced retention of DNA (Ramaswamy, S., et al. The role of organ level conditioning on the promotion of engineered heart valve tissue development in-vitro using mesenchymal stem cells. 2010 February; 31(6):1114-25). Moreover, we identified fluid-induced oscillatory shear stresses a potential mechanism responsible for enhanced de novo collagen formation using mesenchymal stem cells. Yet, in the context of heart valve tissue engineering, it still remains unclear if the exact reproduction of every aspect of native valve dynamics is required or for that matter, required for mechanical conditioning. For optimization purposes, the cell type(s), scaffold materials and related properties, biochemical constituents of the culturing media, and the specific stress modalities (valves are subject to coupled fluid, tensile and flexural stresses) are of primary importance. A precursor to organ level valve conditioning studies therefore may require the development of a device capable of efficiently evaluating several seeded-scaffold specimens in closely controlled, mechanistic studies.

To this end, the effects of individual and combined stress states together with different scaffold materials and cell sources can be systematically evaluated in terms of outcomes such as bulk protein content, differentiation capacity, engineered tissue mechanical properties, cellular signaling events, all that may elucidate how external mechanical factors modulate cell to extracellular matrix interactions. These studies can lead to the development of optimal in vitro conditioning protocol with the specific intent of mechanically stimulating engineered tissue formation (Sacks, M. S., et al. Bioengineering challenges for heart valve tissue engineering. Annu Rev Biomed Eng, 2009. 11: p. 289-313). To achieve this task, we have developed several bioreactors (Engelmayr, G. C., Jr., et al. A novel flex-stretch-flow bioreactor for the study of engineered heart valve tissue mechanobiology. Ann Biomed Eng, 2008. 36(5): p. 700-12; Engelmayr, G. C., Jr., et al. Cyclic flexure and laminar flow synergistically accelerate mesenchymal stem cell-mediated engineered tissue formation: Implications for engineered heart valve tissues. Biomaterials, 2006. 27(36): p. 6083-95; Engelmayr, G. C., Jr., et al. The independent role of cyclic flexure in the early in vitro development of an engineered heart valve tissue. Biomaterials, 2005. 26(2): p. 175-87; and Engelmayr, G. C., Jr., et al. A novel bioreactor for the dynamic flexural stimulation of tissue engineered heart valve biomaterials. Biomaterials, 2003. 24(14): p. 2523-32), and in particular a device that permitted coupled or decoupled flow, stretch, and flexure (FSF) on rectangular scaffold specimens (Engelmayr, G. C., Jr., et al. Ann Biomed Eng, 2008. 36(5): p. 700-12). The rationale of a FSF bioreactor was to enable focused efforts on investigating the effects of innate stress states found in native heart valves to engineered tissue development. Although subsequent studies using this version of the FSF bioreactor determined that the fluid-induced stresses were in the sub-physiological range, combined cyclic flexure and sub-physiologic shear stress conditioning were found to synergistically accelerate tissue production (Engelmayr, G. C., Jr., et al. Cyclic flexure and laminar flow synergistically accelerate mesenchymal stem cell-mediated engineered tissue formation: Implications for engineered heart valve tissues. Biomaterials, 2006. 27(36): p. 6083-95). We were also able to provide more evidence (Ramaswamy, et al. 2010 February; 31(6):1114-25) that the cylindrical shape of the flexure in rectangular shaped FSF bioreactor specimens was analogous to the generic shape of TEHV leaflets.

SUMMARY

We thus identified the need to develop a new bioreactor system capable of developing physiologically relevant fluid-induced shear stresses and regionally specific flow patterns to scaffold specimens and couple these stresses to cyclic flexure and/or stretch states if desired. Here, we describe a device that incorporates several novel features, both in terms of device configuration and in translation, from concept to manufacture, in order to be able to perform these key functions. The device is compact enough to fit in a standard incubator and is composed of easily-interchangeable modular subunits that facilitate use and cleaning. In one embodiment, the device is amenable to MRI analysis, simplifying data acquisition.

A tissue conditioning bioreactor module is provided. The module comprises: a module body comprising a cylindrical, folded passage having a substantially constant diameter ranging from 10 mm to 20 mm, 12 mm to 14 mm or approximately 13 mm, the passage comprising an inlet, an outlet, an upstream portion, a bend, and a downstream portion that widens at a junction to define a cassette compartment with a diameter greater than that of the bend and the upstream portion and further comprising one or more actuator passages extending from the cassette compartment to outside the module body; and a tissue cassette comprising a tube having an inside diameter that is the same as or substantially the same as the diameter of the cylindrical passage, an outside diameter, a lumen and an outside surface, the tube being fluidly connected to the downstream portion of the passage and the outlet of the passage and defining a gap between the outer surface of the tube and the chamber, the cassette further comprising one or more tissue anchor pairs extending through the lumen of the tube, where each pair comprises a movable anchor and a fixed anchor, where the moving anchor passes out of the tube through openings in the tube into the gap and are mechanically coupled to one or more actuators that extend through the actuator passages and outside the module such that movement of the actuator moves the movable anchor relative to the fixed anchor.

In certain embodiments, the movable anchors, such as pins extending across the lumen of the tube, are attached to an annular member slidably disposed in the gap about the tube and connected to the movable anchor and the one or more actuators such that movement of the actuator slides the annular member along the tube thereby moving the movable anchor within the tube. In one embodiment, the bend is approximately 180 degrees.

The module may be manufactured from virtually any material, that is preferably sterilizable. In one embodiment, the module comprises no magnetic parts so that it may be placed in an MRI machine. The material may be a sterilizable MRI-compatible polymer composition, such as a polyetherimide, a polyimide, a polyether ether ketone (PEEK) or a polyethylene. When in use, the module also comprises a bioscaffold attached to a pair of adapters for engaging the movable and fixed anchors. In one embodiment, the cassette is removable from the module to facilitate cleaning the module and mounting of specimens in the module.

In one embodiment, a device is provided for conditioning tissue. The device comprises a base, one or more of the modules described above or herein, and a reciprocating motor mechanically coupled to the actuators of the one or more modules such that reciprocation of the motor moves the actuators, which move the moving anchors within the tube in the module. In another embodiment, the device further comprises a media reservoir, a pump fluidly connected to the media reservoir and the inlet of the one or more modules and a pump controller for controlling pump speed and timing. In a further embodiment, the outlets of the one or more modules are fluidly connected to the media reservoir so that media passing from the reservoir to the module is returned to the media reservoir.

A method also is provided for conditioning a tissue sample. The method comprises attaching the tissue sample to a pair of adaptors for engaging the movable and fixed anchors, mounting the bioscaffold or tissue sample into the module described above and herein, and passing media through the module at laminar flow rates. For example, the media is passed through the module at a flow rate that produces a Reynolds number of less than 2,300. In another example, the media is passed through the module at a flow rate that produces a shear stress of between 5.0 and 24 dynes/cm$^2$. In one embodiment, the tissue sample is an engineered heart valve leaflet material.

BRIEF DESCRIPTION OF THE DRAWINGS

The following Figures are exemplary and are not intended to be limiting.

FIGS. 1A-1G depict schematically one non-limiting embodiment of a bioreactor module as described herein. FIG. 1B is an expanded view of a portion of FIG. 1A viewed from the side. FIG. 1C is an expanded view of a portion of the module of FIG. 1A viewed from the top. FIG. 1D shows the insert assembly of FIG. 1A. FIG. 1E is a cross-sectional view of the assembly of FIG. 1D at 1D. FIG. 1F is an alternate embodiment of the assembly of FIG. 1D where the anchors are disposed centrally within the tube. FIG. 1G shows a tissue sample mounted on spring adaptors prior to insert into the bioreactor module. FIG. 1H shows the tissue sample of FIG. 1F mounted within the bioreactor module (tube is omitted for clarity).

FIG. 9—5-hour variation of (a) pH, (b) $pCO_2$ and (c) $pO_2$ levels after placement in incubator.

FIG. 10—Histological results of the sterility tests of media after 5 days of incubation. PAS positive control image reproduced with permission from "Histotechnology—A Self-Instructional Text" by Carson F L, (2007), page 192, Image 10-11 (Ramaswamy, S., et al. Design of a novel, MRI-compatible bioreactor for longitudinal monitoring of mechanically conditioned engineered cardiovascular constructs. in *International Society for Magnetic Resonance in Medicine, 17th Scientific Meeting*. 2009. Honolulu, Hi.).

DETAILED DESCRIPTION

Figure 1A:
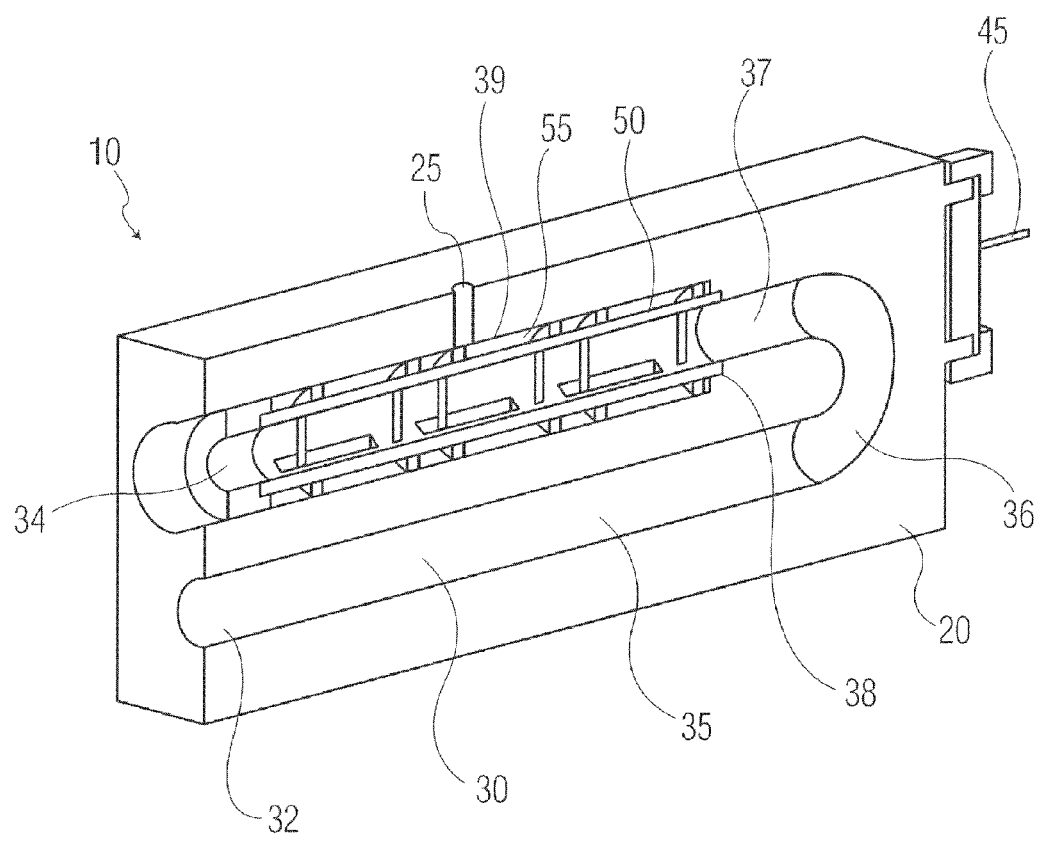

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of these ranges is intended as a continuous range including every value between the minimum and maximum values. For definitions provided herein, those definitions refer to word forms, cognates and grammatical variants of those words or phrases. "Comprising" and like terms are open-ended. The terms "a" and "an" refer to one or more A tissue-conditioning device is provided comprising one or more bioreactor modules comprising a module body. The module body comprises a cylindrical passage (or substantially cylindrical) ranging from 10 to 20 mm, 12-15 mm, or in one preferred embodiment 13 mm in diameter. The passage has a substantially constant diameter. As the object of the passage and its cylindrical profile is to achieve and maintain laminar flow with maximal wall-to-center flow differential, the passage and tube are at least substantially cylindrical and have at least a substantially uniform diameter such that inconsistencies in diameter or circular cross-section do not disrupt or diminish laminar flow and development of maximum shear stress to any substantial extent as fluid travels through the passage and tube. The passage is folded, meaning it has one or more bends that reduce the overall dimensions of the module and rendering it more compact than would be the case if the passage was linear. For example, the bend or bends are may be any angle, taken individually, but result in a three-dimensional pathway through the module body that requires the module to have smaller linear dimensions in one or more dimension; with the overall goal producing a more compact module as compared to a module in which the pathway is linear (not folded). The angle of each bend would typically range from 90 to 180 degrees, for example a bend of from approximately 135 to 200 degrees, and in one embodiment approximately 180 degrees ("U-shaped"). The bends also can result in a three-dimensional pathway, as compared to the two-dimensional passage (a simple "U-shape") as depicted in FIGS. 1A-1D, below.

The passage has an upstream portion (in relation to a flow direction) comprising a fluid inlet, upstream to the bend and a downstream portion (in relation to a flow direction) and a fluid outlet, downstream to the bend, one or more pairs of tissue anchors disposed within the downstream portion of the passage, where at least one anchor from each pair is movable in relation to the other, non-movable anchor of the pair, and an actuator connected to the movable anchor. Note that the "actuator" in Example 1 is referred to therein as an axial rod or axial rail, but an "actuator" is used herein as a mechanical coupling between a reciprocating motor and the movable anchor. The reciprocating motor includes as a class of motor known as a "linear actuator" as mentioned in Example 1 as well as rotating motors that are mechanically coupled (via the "actuator" rods, rails, etc.) to the movable anchor to move the movable anchor relative to the non-movable (fixed) anchor. By mechanically coupled, it is meant the components are attached either directly or indirectly such that a desired mechanical effect is accomplished, such as is the case of mechanically coupling the motor to the actuator to move the actuator. In certain embodiments, the device comprises a motor attached to the actuator for moving the actuator to cause the movable anchor of the anchor pair to move within the passage relative to the other anchor of the anchor pair, a pump fluidly connected to the fluid inlet of the upstream portion of the passage, and a fluid reservoir fluidly connected to the pump and the outlet of the downstream portion. Fluid is passed through the passage at below a Reynolds number of 2300 to achieve laminar flow through the passage. The passage is substantially cylindrical, meaning that a cross-section of the passage is substantially circular. Using a circular passage maximizes shear between the middle of the passage and at its walls, resulting in a maximum ratio of about two as opposed the about 1.5 for rectangular passages. The device and methods described herein easily meet physiological shear stress levels of from 5.1-8.6 dynes/cm$^2$ at moderate flow rates (e.g., 0.8 to 0.9 L/minute, and can reach up to about 24 dynes/cm$^2$ at the surface of the samples within the device, as depicted in the examples below.

The passage is bent (folded) principally for producing a compact modular structure that, for example and without limitation, can fit in a typical incubator. As shown in the examples below, in one embodiment, the passage is folded in half (that is the passage is bent 180 degrees) such that the path within the module is sufficiently long to develop maximal laminar flow differential across the radius of the circular profile of the passage. The path may include two or more bends, resulting in more compact designs. For example, the modules may be half as long as those depicted in the Figures and Examples below, if the passage comprises three bends of 180 degrees. Of course, in reference to the designs depicted in the Figures, shortening the overall length of the module may reduce the number of samples that may be contained within the module at any given time.

The module and its components may be manufactured from any useful material that does not negatively impact the ability of cells to grow and tissue to survive or propagate within the passage. The material should be able to withstand sterilization treatments, such as autoclaving, gamma irradiation or ethylene oxide treatments. In one preferred embodiment, the module and its components are compatible with magnetic resonance imaging methods useful in imaging the tissue structures within the passage (an "MRI-compatible" material). One such material is polyetherimide (e.g., ULTEM™), an amorphous thermoplastic polyetherimide, which also is available as a polymer blend. All plastics can be put in an MRI machine, some create artifacts, such that the images don't look as good. Along with ULTEM™, another commercially-available polymer composition that is expected to be particularly useful are VESPEL® polyimide resins (Dupont). Although ULTEM™, and PEIs and polyimides in general, are polymer compositions that are considered by some to be superior for MRI owing to their excellent magnetic resonance susceptibility match to water, other classes of plastics that are expected to work include polyether ether ketones (PEEK) and polyethylenes. Although virgin polyimide polymer-containing compositions (e.g., ULTEM™ and VESPEL®) are useful, polyimide compositions comprising certain additives also are expected to be useful, including polyimide compositions comprising: graphite (e.g., 15%-40% graphite by weight, including 15% graphite by weight and 40% graphite by weight); polytetrafluoroethylene (PTFE or TEFLON®) and graphite (e.g., 10% PTFE and 15% graphite by weight); and molybdenum disulfide (e.g., 15% by weight).

The embodiments of the device and related methods are exemplary and given the teachings herein, a person of ordinary skill in the engineering arts can produce equivalent variations of the designs presented herein and such designs are considered to be within the scope of the present invention.

FIG. 1A provides a cross-sectional view of one embodiment of a module 10. The module 10 is manufactured from any useful composition, such as polyetherimide. The module body 20 comprises an injection port 25 and a passage 30. Passage 30 comprises an inlet 32 at its upstream end and an outlet 34 at its downstream end. Passage 30 comprises an upstream portion 35, a bend 36 (a 180 degree bend as depicted), and a downstream portion 37. Downstream portion 37 widens at a junction point 38 into a cassette compartment 39 having a diameter greater than that of the rest of the passage 30 (that is as compared to the diameter of the bend 36 and the upstream portion 35). A tube 50 is disposed within the cassette compartment 39.

Figure 1B:
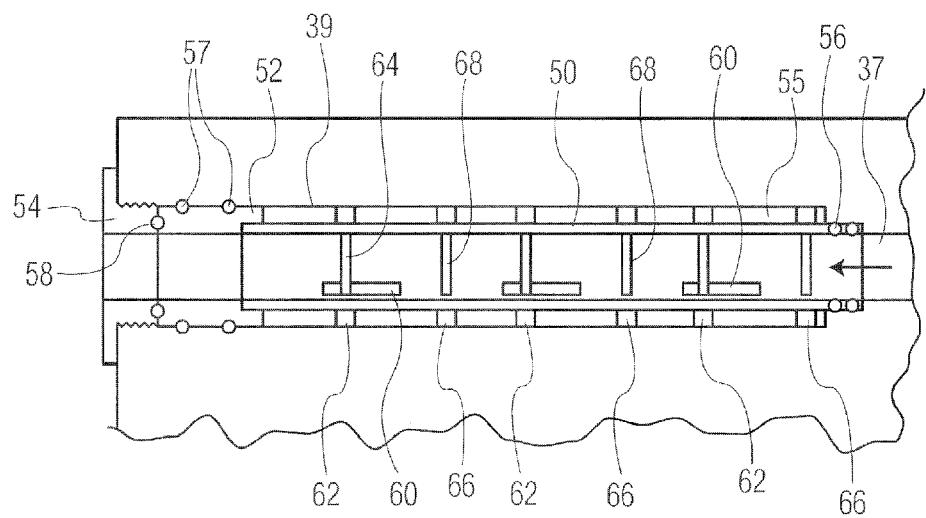
Figure 1C:
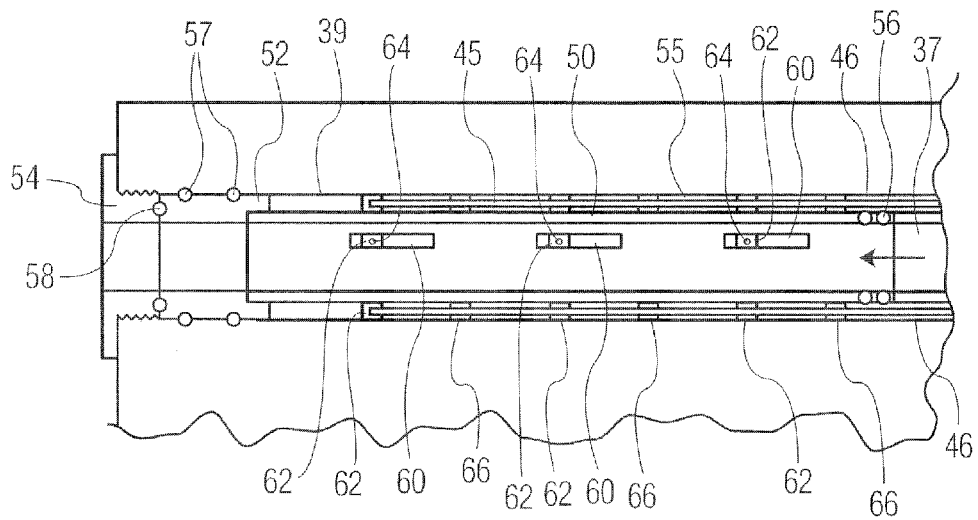

FIG. 1B depicts an expanded view of the downstream portion 37 of the passage 30, including the cassette compartment 39. As indicated in reference to FIG. 1A, a tube 50 is disposed within the cassette compartment 39. The tube has a lumen and an outer side that defines a gap 55 with the wall of the cassette compartment 39 of the passage 30. The tube is cylindrical (having a circular cross-section) and has a lumen diameter that is approximately the same and preferably the same as the diameter of the upstream portion and bend 35 and 36 so as to not interrupt the laminar flow of fluids within the passage 30 and the tube 50. The tube 50 comprises six slots 60 in three opposing pairs. Six annular members (rings) are disposed about the outer side of the tube 50 within the gap 55. Three movable rings 62 are slidably disposed about the slots 60, meaning they are able to slide within the gap 55 along the tube 50. A movable anchor pin 64 is attached to each movable ring 62 and passes through the slots 60 and lumen of the tube 50. FIG. 1C shows the same structure as FIG. 1B except from a top view in order to depict a plurality of actuators 45 that are attached to each movable ring 62 (see FIG. 1D for further detail), and which pass through holes in non-moving rings 66 and pass through holes 46 that extend to the exterior of the module body 20 and are movable within the holes in non-moving rings 66 and holes 46 such that movement of the actuators 46 move the movable rings 62. Each non-moving ring 66 is attached to a non-moving anchor pin 68 that passes through the lumen of the tube 50. Anchor pins 64 and 68 can be removed from the lumen of the tube 50 to permit insertion of a specimen into the module 10.

The insert assembly of the module, comprising the tube 50, rings 62 and 64, pins 64 and 68 and actuators 45, can be removed from the module 10 to facilitate cleaning of the module components and loading of the module with a test sample. Anchor pins 64 and 68 are inserted into holes in the rings 62 and 66 and can be held in place by friction or by threading (screw), in which case an end of the pins will have a slot, star (Philips head) or other useful adaptation to facilitate screwing the pin into place. Tube 50 comprises at its downstream end an annular centering member 52 and is held in place by a cap 54 that is shown as being threaded into the module 10, though any other method may be used to hold the cap in place, such as screws, latching members, etc. Junction 38 is slightly wider than an outer diameter of the tube 50 such that the tube 50 can be inserted into the junction 38. The junction 38 also is depicted as having two annular grooves in which two o-rings 56 are seated. Annular centering member 52 is depicted as having two annular grooves into which o-rings 57 are inserted. Likewise annular centering member 52 also comprises a circular groove about the opening in its downstream end into which an o-ring 58 is seated, so that it can form a seal with the cap 54 when the cap is in place. Of note, actuators 45 pass through the body 20 of the module 10 and can be sealed to prevent liquid from escaping the module by use of o-ring about the actuators or any useful sealing method.

Figure 1D:
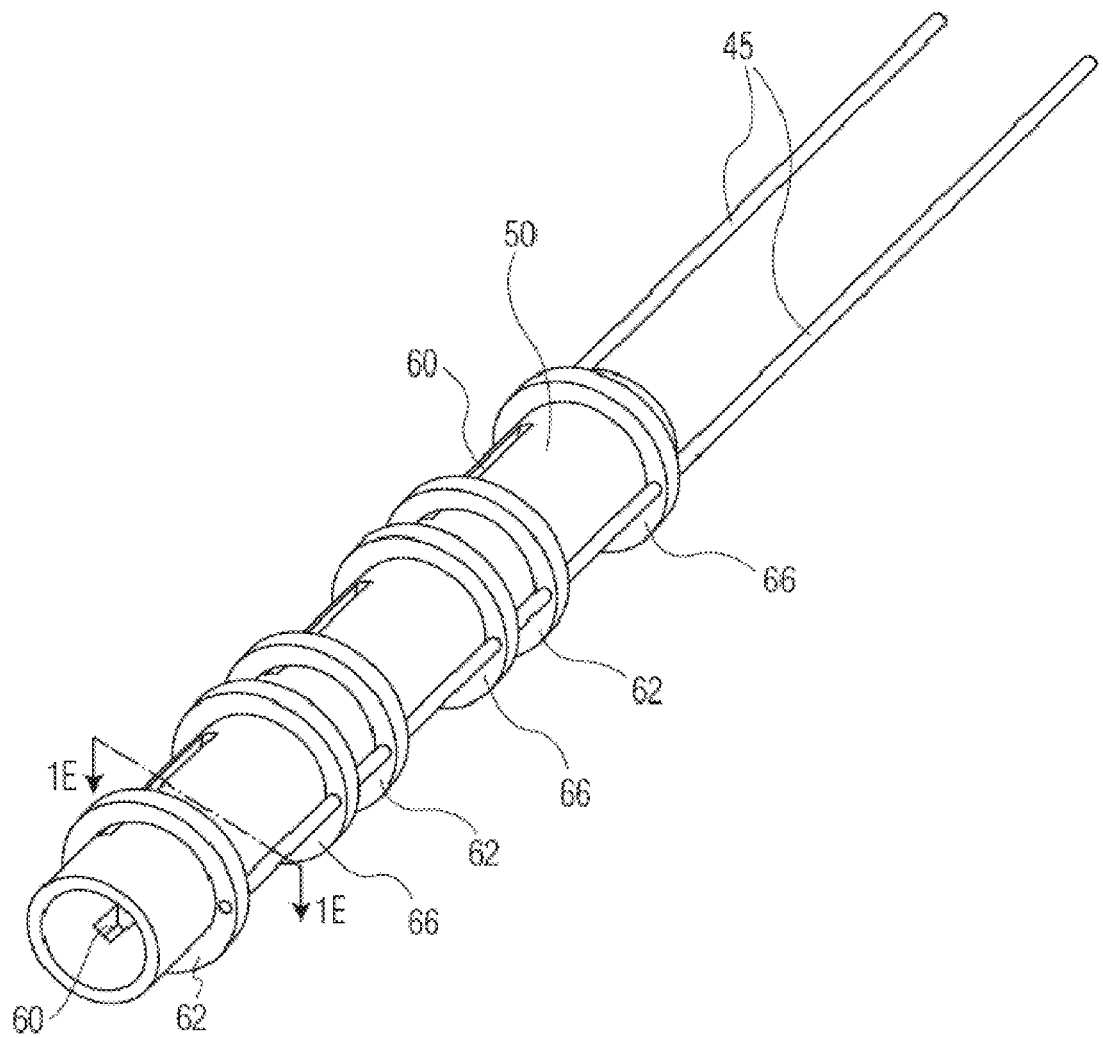

FIG. 1D shows the tube 50, actuators 45, rings 62 and 66 and slots 60 removed from the cassette compartment 39 of the module. Movable rings 62 can slide along the tube 50, but are limited in their movement by the length of the slots 60 when pins are in place and are attached to actuators 45. Non-movable rings 66 cannot slide along the tube 50 and are either fixed to the tube 50 or held in place about holes in the tube 50 for receiving the pins 68 through the lumen of the tube. Actuators 45 pass through holes in non-movable rings 66 and can slide within the holes so that the movable rings 62 can be moved. In FIG. 1D, the slots 60 and pins 64 and 68 do not pass through the center of the tube, as shown in FIG. 1E, which is a cross-section of the assembly at "1D". FIG. 1F shows an alternate embodiment to that of FIGS. 1D and 1E, with the pins 64 centered within the tube 50.

FIG. 1G shows two spring members 80 attached to a bioscaffold 82. The bioscaffold 82 can be mounted within the tube 50 by removing pins 64 and 68 from rings 62 and 66, respectively, inserting the bioscaffold 82 or other tissue sample into the lumen of the tube 50 and aligning the spring members within the tube 50 such that the pins 64 and 68 can pass through the center of the spring members 80 when re-inserted into the rings 62 and 64 (see FIG. 1H, which omits the tube for clarity). The pins 64 and 68 are re-inserted into the rings 62 and 64 and the insert assembly is then placed into the cassette compartment 39. Spring members 80 may be any suitable structure or adaptor for engaging both the bioscaffold 82 and the anchors 64 and 68, and can be springs, rings, loops, tubes, clips, etc. Springs are useful because they can be threaded into a tissue sample by twisting and also are able to engage the pins by inserting the pins axially through the spring.

Figure 2:
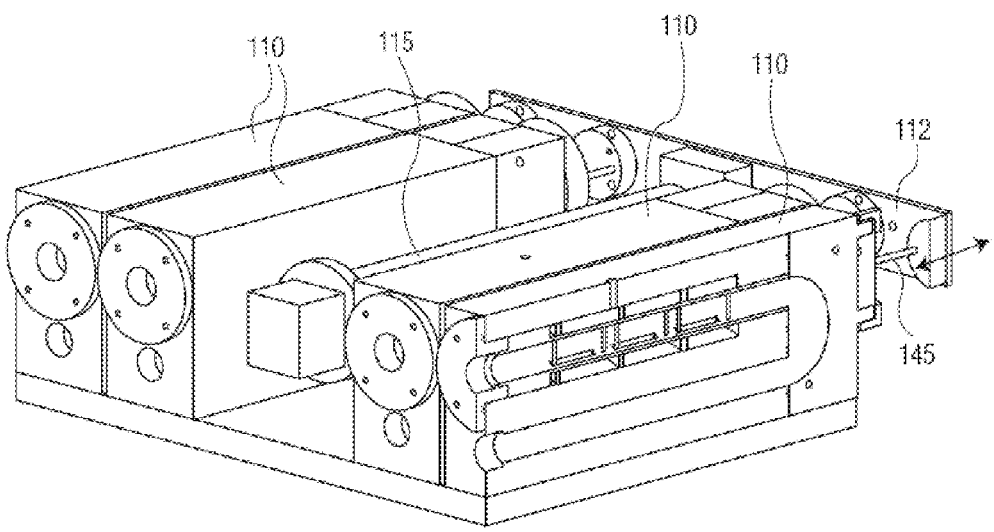
FIG. 2 depicts schematically four bioreactor modules such as the modules of FIGS. 1A-1G assembled into a non-limiting embodiment of a modular bioreactor system as described herein.

FIG. 2 shows a device comprising multiple modules 110 as depicted in FIGS. 1A-1F. Actuators 145 are attached to bar 112, which is attached to a reciprocating (linear) motor 115 which moves the actuators 145 in relation to the modules 110, thereby moving the movable rings and anchor pins within the module 110.

Figure 3:
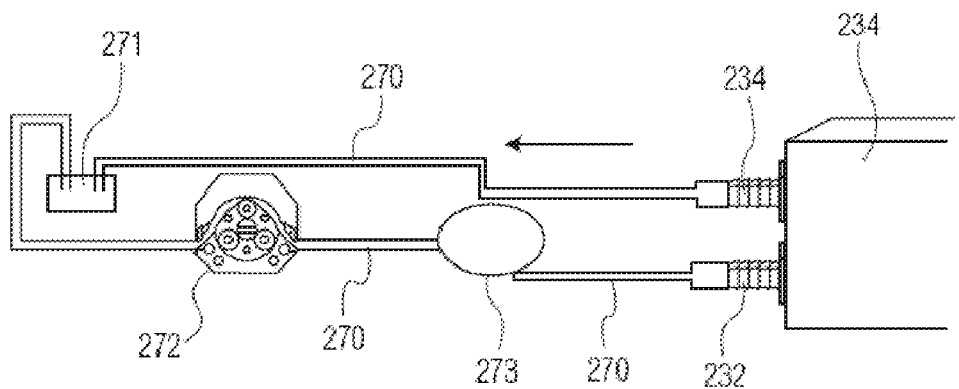
FIG. 3 depicts schematically one non-limiting embodiment of a bioreactor system as described herein.

FIG. 3 depicts a complete system 200 comprising a module 210 having inlet and outlet barbs 232 and 234, respectively, tubes 270 for fluidly coupling the elements of the system 200, a media reservoir 271, a peristaltic pump 272, and a pulse dampener 273 forming a closed loop circulation system. Media for the media reservoir can be any suitable fluid for growing, propagating, maintaining or otherwise contacting a tissue sample, such as a bioscaffold, within the module 210, and it includes, without limitation cell growth media, such as DMEM; buffer solutions, such as PBS; blood; blood fractions; and blood substitutes.

The pump may be any suitable pump, but in one embodiment, the pump is a peristaltic pump as finds use in the medical industry. A typical magnetic impeller pump does not have the ability to pump more viscous fluids and is not as precisely controllable as a peristaltic or dosing pump. The pump should have an output within a range that provides sufficient flow rates to produce adequate shear forces in the passage of the module. As indicated above, the flow velocity should produce laminar flow, typically found with velocities generating a Reynolds number of less than about 2,300. The pump can be controlled by any suitable method, for instance with a computer (digital) or analog control module or device, as are broadly available. A large variety of methods for varying pump speed over time are known in the engineering arts.

As described above, the insert assembly, comprising the cap, tube, rings and actuator rods, is removed from the module. A tissue sample, such as a bioscaffold is attached to two annular mounts which have inside diameters greater than that of the anchors. The anchors are removed (pulled, unscrewed, etc.) from the tube. The tissue scaffold is placed within the tube and the anchors are passed through the annular mounts and are fixed (e.g., screwed or otherwise mounted) in place relative to the tube. The tube, is replaced within the module and the cap is attached, thereby sealing the module. The actuators are attached to the motor and fluid, such as cell growth medium, is pumped through the module. The fluid can be pumped continuously or periodically for any desirable or suitable time period(s) and likewise, the actuator(s) may be moved to flex the scaffold continuously or periodically to any desired or suitable time constraint and an any desirable or suitable amplitude (distance the movable anchor moves relative to the other anchor in the anchor pair). As used herein the term "tissue sample" includes native tissue (obtained from an organism), engineered bioscaffolds comprising a cell scaffold from natural constituents (e.g., decellularized extracellular matrix or components thereof, such as collagen) and/or synthetic components, such as polylactic acid (PLLA) and polyglycolide (PGA) (co)polymers, such as is described in Example 2 and poly(ester urethane) urea (PEUU) and poly (ether ester urethane) urea (PEEUU). Cells are typically disposed within and/or on the bioscaffolds.

The Examples below are provided to illustrate embodiments of the invention and are not intended to limit the scope of the invention in any way.

Example 1

A Novel Bioreactor for Mechanistic Studies of Engineered Heart Valve Tissue Formation Under Physiological Conditions In studies of heart valve tissue engineering, to date no bioreactor offers the possibility of both coupled/decoupled flow-stretch-flexure (FSF) stress states, exerted on in-vivo heart valve leaflet tissues and the ability to replicate the physiological hemodynamic conditions. To achieve these design goals, we implemented a narrow, cylindrical conduit configuration to design a new FSF bioreactor conditioning chamber so that higher fluid velocities at the pipe core could be obtained, translating to higher shear stresses on the in-situ tissue specimens while retaining laminar flow conditions.

Computational fluid dynamic simulations were performed to predict the flow field under various specimen configurations, flow rates and viscosities. The device was successfully constructed and tested for incubator housing, gas exchange and sterility. Typical range of surface-specimen fluid-induced shear stress magnitudes that can be generated by the device is in the order of 0-24 dynes/cm$^2$. For tissue formation studies concerning engineered heart valves, normal physiological levels of mean shear stresses under laminar flow, in the range of 5.1 to 8.6 dynes/cm$^2$ experienced by native heart valves is achieved in this bioreactor, using regular cell culture media without the need for viscosity-increasing additives. The implications of this are that coupled or decoupled physiological flow, flexure and stretch modes of engineered tissue conditioning investigations can be readily accomplished with the inclusion of this device in experimental protocols on engineered heart valve tissue formation.

Methods

Design

Three fundamental requirement for the bioreactor include a sterile culture environment, physiologically realistic conditions as related to heart valve function, and relative ease of use to facilitate the handling of sterile specimens (Hildebrand, D. K., Design and Evaluation of a Novel Pulsatile Bioreactor for Biologically Active Heart Valves, in *Bioengineering.* 2003, University of Pittsburgh: Master's Thesis). In particular, the ability to provide a bio-mimetic stress environment to evolving tissue specimens is considered critical, but still has yet to be sufficiently delineated or understood in terms of regional stress distribution effects on the tissue formation rates. We were nonetheless able to provide some supportive evidence of this requirement, showing that physiological fluid pressure levels (mean pressure=20 mm Hg) as a means to mechanically condition dynamic tri-leaflet engineered heart valves resulted in a 35% increase in the rate of collagen production per scaffold-seeded cell versus experiments performed under non-physiologic conditions (Ramaswamy, et al. 2010 February; 31 (6):1114-25).

The physiologic range of fluid-induced shear stresses was initially identified in polyurethane valve leaflets between 10-17 dynes/cm$^2$ at a flow rate of 7.5 L/min (Weston, M. W., et al. Estimation of the shear stress on the surface of an aortic valve leaflet. Ann Biomed Eng, 1999. 27(4): p. 572-9); more recently, precise computations of the shear stresses on native aortic valves (Sacks, M. S. et al. Heart valve function: a biomechanical perspective. Philos Trans R Soc Lond B Biol Sci, 2007. 362(1484): p. 1369-91) were found to be in the order of 5 to 6 dynes/cm$^2$ on the ventricular side and <1 dynes/cm$^2$ on the aortic side. While the ideal shear stress environment in the context of an optimum TEHV conditioning protocol are still uncertain, it would thus seem that there would be a rational physiological basis to generate mean shear stress magnitudes with an upper limit of 6 dynes/cm². Regional shear stress variations would subsequently be dictated by the specimen geometry and configuration. The following more complete design criteria were developed for the device, which allowed for the incorporation of a wide array of mechanistic studies related to TEHV development:

Provide a sterile environment for tissue growth.
Capable of adequate gas exchange.
House multiple tissue specimens.
Can be placed in a standard cell culture incubator.
Provide flow, stretch and flexure stress conditioning separately or in any combination.
Be adapted to be MRI compatible for longitudinal cell and/or tissue tracking studies.
Utilize either steady or pulsatile flow regimes.

The chamber geometry is critical in inducing physiological levels of fluid-induced shear stresses on the specimens. This was possible by basic fluid mechanical considerations as follows. The main chamber of the FSF bioreactor was a narrow cylindrical tube, where the Reynolds number (RE) is given by:

$$RE = \frac{\rho v D}{\mu} \quad (1)$$

where $\rho$ is the fluid density, $\mu$ the dynamic viscosity, v is the mean fluid velocity and D is the cross sectional diameter of the chamber. For a Newtonian fluid, the relation between the fluid shear stress ($\tau$) to the velocity is:

$$\tau = -\mu \frac{dv_x}{dy} \quad (2)$$

where $v_x$ is the fluid velocity in the horizontal direction and y is the vertical direction in a conventional Cartesian coordinate system. Note that laminar flow generally holds for RE<2300, so that a small cross-sectional diameter would facilitate higher fluid velocities (and hence fluid-induced shear stresses) at a given RE number. Large diameters, while facilitating the insertion of specimens into the device would greatly reduce the ability to keep the flow within the laminar range if physiological levels of shear stresses were desired. Finally, the maximum velocities ($V_{max}$) in a cylindrical tube versus a chamber with a rectangular cross-section are given by:

$$V_{max}=2v \quad (3)$$

and $$V_{max}=1.5v \quad (4)$$

As a result, a circular cross-section allows enhanced flow development capabilities (ultimately, ~33% higher) over rectangular cross-sections and would result in higher shear stresses when specimens were placed in the path of the centerline velocity in the bioreactor chamber. A final diameter, D=13 mm was determined based on what we computed to be the smallest diameter possible that would concomitantly not interfere with specimen insertion and was practical for fabrication.

Adequate dynamic range in flow rate was necessary for the pump component of the bioreactor. In addition, the flow source would have to be capable of driving more viscous liquids (e.g. blood viscosity) in an efficient manner so as to achieve further increases in fluid-induced shear stress levels on the surface of the housed specimens, e.g. from 0.89 cP (water)≤µ≤4 cP (blood). To accomplish this task, we chose to use a peristaltic (i.e., roller) pump (Masterflex, Cole-Palmer, Vernon Hill, Ill.) capable of flow rates up to 2.3 liters/min (LPM).

Computational Fluid Dynamics

In the bioreactor, specimen flexure was induced utilizing an actuator connected to a moving post that is in turn connected to one end of each sample, with the other end connected to a fixed post. As the actuator moves, the moving post moves a certain distance towards the fixed post resulting in a bent configuration. We observed that the flexure of rectangular scaffold strips in the FSF bioreactor take on a parabolic shape. Additionally we assumed that the sample along its length (x-direction) conformed to the equation of an arc length (equation 5) with the constraint of a fixed length (L) at any time point of 25 mm.

$$\int_a^b \sqrt{1+(2Cx)^2} dx = L \quad (5)$$

where a is the position of the fixed post, b is the evolving position of the moving post that moves towards the stationary post (determined from the prescribed actuator motion) and C is the nonlinear constant that changes according the new position b with each time step. The above integral was computed in Mathcad v.14 (PTC, MA, USA) to determine the values of C over a 1 Hz cycle (fully straight to maximum flexure to fully straight again) over 500 time steps.

Viscosity and Flow Rate Studies.

Apart from the geometry of the conditioning chamber of the FSF bioreactor, the media viscosity and pump flow rate parameters play a central role in the magnitude of fluid-induced surface shear stresses that can be generated on housed specimens. Viscosity measurements were thus conducted on two possible scenarios of tissue culture: 1) Control (standardized) media used in our previous TEHV protocols (Ramaswamy, et al. 2010 February; 31(6):1114-25) and 2) increased-viscosity media. Control Media (Dulbecco's modified Eagle's medium (DMEM) supplemented with 10% fetal bovine serum, 1% antibiotic-antimycotic plus HEPES buffer (all purchased from Invitrogen, Carlsbad, Calif.), 82 µg/ml ascorbic acid-2 phosphate (Sigma, St. Louis, Mo.) and 2 ng/ml basic fibroblast growth factor (Peprotech, Inc., Rocky Hill, N.J.) was prepared and filter sterilized (Nalgene Inc, Rochester, N.Y.).

For studies focusing on the effects of fluid shear stress on live cells and tissue, standard culture media has been previously augmented with Dextran (Li, D., et al. Effects of dextran on proliferation and osteogenic differentiation of human bone marrow-derived mesenchymal stromal cells. Cytotherapy, 2008. 10(6): p. 587-96) or Xanthan Gum (van den Broek, C. N., et al. Medium with blood-analog mechanical properties for cardiovascular tissue culturing. Biorheology, 2008. 45(6): p. 651-61) to mimic blood viscosity. As previously utilized (Id.), 0.69 g/L of Xanthan Gum (Sigma) was added to the control media to create blood-analog fluid viscosity. A Brookfield cone and plate rotational rheometer (Middleboro, Mass.) operating at 25° C. was used to measure the viscosity of the media samples (3 samples/group) over various shear rates from 50 to 700 s⁻¹.

Computational fluid dynamic (CFD) models were developed (Fluent CFD software, Ansys Inc, Lebanon, N.H.) in order to predict the flow physics in the bioreactor chamber. Initial CFD models utilized the viscosity material properties (1.3 cP and 3.7 cP respectively) that were determined for control media and Xanthan Gum-augmented media (See Results section) to compare the effects of different viscosities on resulting fluid-induced shear stresses on FSF-bioreactor specimens. Previously reported (Engelmayr, G. C., Jr., et al. Ann Biomed Eng, 2008. 36(5): p. 700-12) density values of 1010 kg/m³ for 10% FBS supplemented DMEM and 1040 kg/m³ for blood were used respectively, at a prescribed flow rate of 1.06 LPM (Re=486). In order to observe the effect of varying the flow rate, in a similar manner, a flow rate of 557 ml/min and a higher flow rate of 850 ml/min, both within the capabilities (0 to 2,300 ml/min) of the pump were set, while retaining the blood material properties. Specimen geometry at the fully flexed state was simulated.

An unstructured mesh consisting of $1.5 \times 10^6$ tetrahedral elements ($2.6 \times 10^6$ nodes) was constructed. Newtonian fluid behavior was assumed in all the CFD models. Steady flow simulations were run since the time-varying nature associated with the cyclic flexure of the specimens would be controlled by an actuator and not by the pulsatility of the flow. 3 specimens (L×W×t=25×7.5×1 mm) in parallel were housed in the device equidistant from each other (37 mm) and positioned 4.3 mm off-center in the tube, so that contact between specimens and the tube inner wall would not occur. At the fully flexed state, the specimens would induce a localized stenosis, the severity of which would be dictated by the specimen dimensions, ultimately resulting in higher surface shear stresses. Hence, the specimen spacing and positioning requirements were specifically chosen to maximize this effect, while at the same time ensuring that the flow would not be adversely obstructed, thereby resulting in sufficient uniformity in the shear stress distribution between specimens.

Specimen Geometry.

The effect of varying levels of specimen flexure on the resulting fluid-induced shear stresses was also investigated. Specimen geometry was discretized at the fully straight (t=0 s), slightly bent (t=50 ms) and the fully bent (t=500 ms) time positions and CFD models of these specific configurations were subsequently simulated. Fluid density of 1040 kg/m³ and a viscosity of 0.0037 dynes-cm/s determined from the viscosity measurements of blood-analog media (see Results section) used to simulate blood-analog material properties were applied. An inlet velocity boundary condition amounting to an RE=486 (flow rate of 1.06 LPM) and an outflow outlet condition was prescribed. Note that in all the CFD models, residual convergence for continuity and motion was prescribed as $<5 \times 10^{-5}$.

Device Concept to Fabrication

Several unique design features in the bioreactor were developed in order to enable assemblage of the device during actual (FIG. 1a). A key criterion that allowed for a small (13 mm) cross-section for the U-shaped fluid enclosure was the ability to incorporate a separate, sliding sample holder (FIG. 1b). This attribute of the device design permitted access of surrounding pins and rings (contained in the outer tube) to the housed specimens, without any possible intrusion to the flow path. In addition, the holder could be separated from the rest of the device and facilitated ease of specimen insertion/removal.

Following the design developed by Engelmayr et al. (Ann Biomed Eng, 2008. 36(5): p. 700-12), we utilized a spiral bound grip for tissue attachment held in place by a pin (McMaster-Carr) (FIG. 1-c). One pin/specimen was fixed while the other pin was allowed to move. This movement was made possible through rings (McMaster-Carr) that are able to slide axially along the outer tube (See, FIGS. 1A-1D). In addition, the rings are coupled (via set screws) to a pair of axial rails (McMaster-Carr) (See, FIG. 1C), which are subsequently connected to a linear actuator (UltraMotion, Mattitick, N.Y., described generically herein as a motor) and can be programmed to prescribe a uniaxial displacement rate. Leakage is prevented at the exit location of the rails with the aid of silicon o-ring seals. The overall system can be accommodated in a standard size cell culture incubator and consists of 4 conditioning chambers for a maximum capacity of 12 specimens (See, FIG. 2). The grips, pins, rings, and axial rails of the bioreactor were all made with 316 grade stainless steel.

Polyetherimide (ULTEM™, General Electric, Pittsfield, Mass.; purchased as ULTEM 1000 resin, McMaster Carr) plastic was used as the material for device fabrication primarily due to its excellent resilience to withstand sterilization (autoclave and ethylene oxide gas) procedures. An added benefit of ULTEM is its ability to provide outstanding magnetic susceptibility matching to water (Doty, D. F., et al. Magnetism in high-resolution NMR probe design. I: General methods. Concepts in Magnetic Resonance Part A, 1998. 10(3): p. 133-156) which permits the bioreactor to be imaged using magnetic resonance imaging (MRI). An effort to facilitate complete MRI compatibility and image the housed specimens in a noninvasive and nondestructive manner by MRI has been demonstrated elsewhere in a prototype version of the device (Ramaswamy, S., et al. Design of a novel, MRI-compatible bioreactor for longitudinal monitoring of mechanically conditioned engineered cardiovascular constructs. in *International Society for Magnetic Resonance in Medicine, 17th Scientific Meeting.* 2009. Honolulu, Hi.). Connectivity of the bioreactor chambers to the peristaltic pump was performed via gas permeable, platinum-cured, silicone tubing (Cole-Palmer) whose length was roughly 2.5 feet from one end of the bioreactor chamber to one end of the pump.

A glass bottle (media volume ~500 ml, VWR, Bridgeport, N.J.) was connected to each chamber (see, FIG. 3) to allow for media exchange which occurs as follows: The peristaltic pump is first used to clear all the spent media from the tubing and the conditioning chambers into the bottles. Next a second pump that is kept outside of the incubator is used to evacuate the media from the bottles into a waste container that is housed within a sterile culturing hood. The process of media removal is then reversed to allow entry of fresh media into the system.

Gas Exchange and pH Measurements

In order to determine the efficiency of gas exchange between the FSF bioreactor and the ambient air inside a standard cell culture incubator, oxygen partial pressure ($pO_2$), carbon dioxide partial pressure ($pCO_2$) and pH measurements were performed using a blood-gas analyzer (Radiometer medical, Westlake, Ohio). The device was gas sterilized with ethylene oxide for 16 hours prior to use. Measurements were conducted under three different experimental settings: i) a chamber with flow (flow rate=1.06 LPM), ii) a chamber with no flow, and iii) a plastic tube with a filtered cap (BD biosciences, San Jose, Calif.) that served as a control. Media (DMEM supplemented with 10% fetal bovine serum, 1% antibiotic-antimycotic plus HEPES buffer, (Invitrogen)) was prepared and filter sterilized (Nalgene Inc, Rochester, N.Y.). The media was introduced to the three groups. An initial measurement was taken immediately after the groups were placed into the incubator (Fisher Scientific, Pittsburgh, Pa.). Measurements from the two FSF bioreactor chamber groups were taken with a syringe through an injection port (see, FIG. 1A) located at the top of the flow chambers. Thus, media was extracted directly at the site where specimens would normally be housed in an experiment. Measurements of $pO_2$, $pCO_2$ and pH were also determined for media from the plastic tube. Media extracts (1 ml volume) were taken for each measurement at half-hour intervals over a 5 hour period. In addition, aliquots (N=3/group) were assessed from each group after 3 days. Statistical significance (P<0.05) was computed using unpaired t-test between the bioreactor-based and control groups.

Sterility Assessment

As a means to evaluate contamination risk in the device, positive/negative gram staining (for common bacteria) and Periodic Acid Schiff (PAS) light green (for common fungal organism detection) histological stains were performed on samples of media that was circulated through the bioreactor. In brief, spent media (after 5 days of operation) from the bioreactor was smeared onto clean slides with a cotton tipped swab. Slides were then fixed in absolute alcohol for 30 seconds after which the stains were applied. Once all histological stains had dried, a yellow background stain was also used to allow for enhanced visibility. The slides were subsequently photographed under view of an optical microscope set to a magnification of ×200.

Results

Media Viscosity

Media viscosity for control media and Xanthan-Gum-augmented media were determined (FIG. 3). The control media was found to be Newtonian (R2=0.974) with an average viscosity of 1.3 cP. On the other hand, the Xanthan Gum-augmented media exhibited Non-Newtonian behavior. Previous FSF bioreactor CFD studies (Engelmayr, G. C., Jr., et al. Ann Biomed Eng, 2008. 36(5): p. 700-12) in our laboratories assumed a blood viscosity of 3.7 cP which was found to occur at a shear rate of ~265s$^{-1}$. The effects of these viscosity material parameters on the flow field were subsequently applied in the CFD models.

CFD Models

CFD simulations were run with the U-shaped tube geometry, housing 3 rectangular specimens (FIG. 4A), that depicted a conditioning chamber of the bioreactor. Solution convergence was achieved at the prescribed residual values for continuity and motion equations (<5×10$^{-5}$). Close inspection of the flow patterns (FIG. 4B) revealed that the off-center positioning of the specimens minimized disruption of the velocity streamlines, which were found to progress smoothly over and around the specimens. This was important as it would ensure that each specimen would be subjected to near-identical velocity and hence fluid-induced shear stress fields. Indeed, this was found to be the case; the velocity field around the FSF-bioreactor specimens increased with increased flexural states (FIG. 5), ranging from 2.5 to 25 cm/s (approximate mean values). Peak velocities occurred near the vertex of the flexed samples where a localized stenosed region was created between the specimens and the adjacent wall of the bioreactor chamber.

Figure 4:
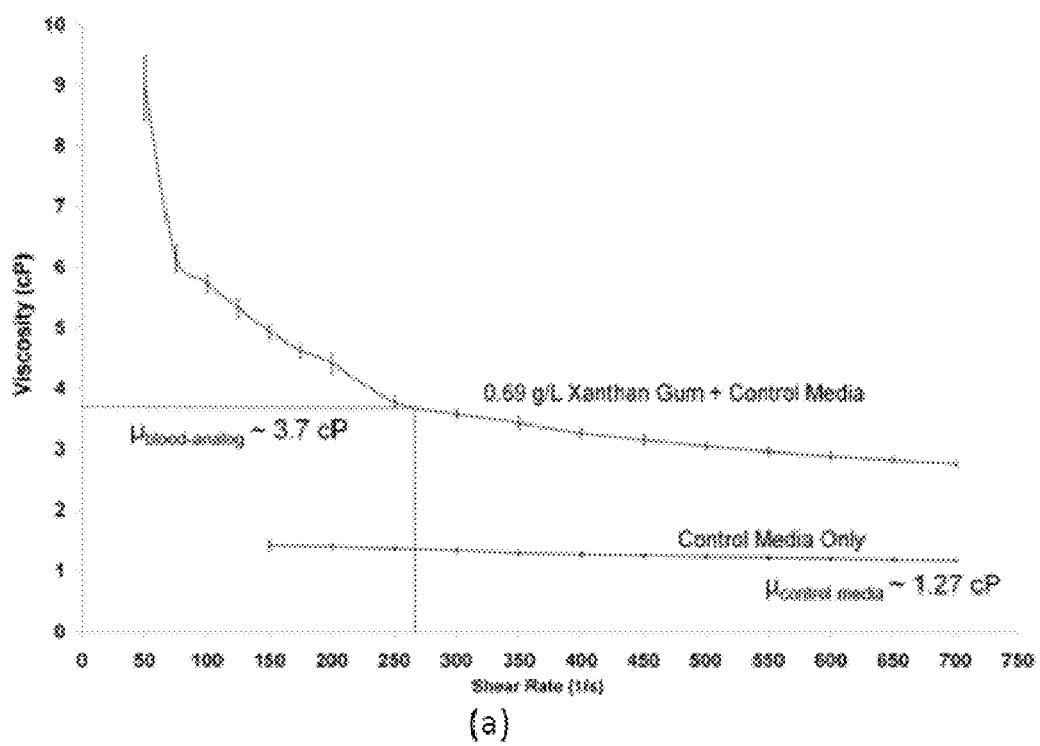
FIG. 4—(a) Viscosity versus Shear Rate measurements for control (regular) cell culture media and increased viscosity media, augmented with Xanthan Gum. Note the respective Newtonian and non-Newtonian behavior of the 2 groups. (b) Velocity streamlines progressing through the bioreactor chamber. Note that the adequate spacing between (by 37 mm) and off-centering (by 4.3 mm) of specimens causes the flow to proceed around and over the housed specimens thus providing more uniformity in shear stress distribution between specimens.
Figure 4:
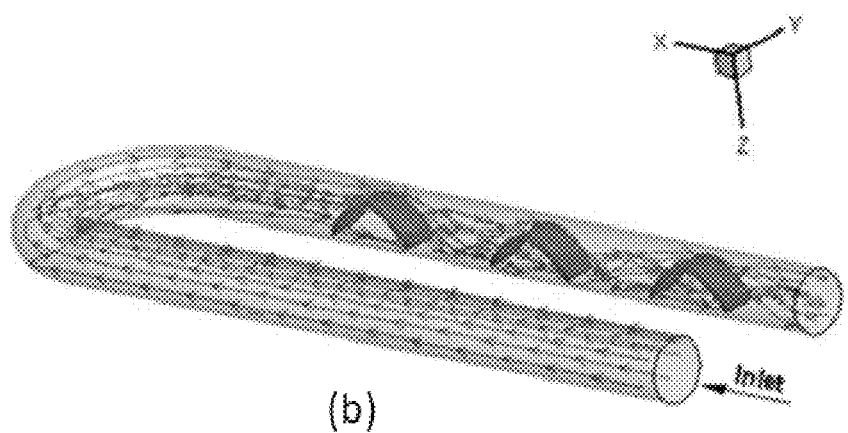
Figure 5:
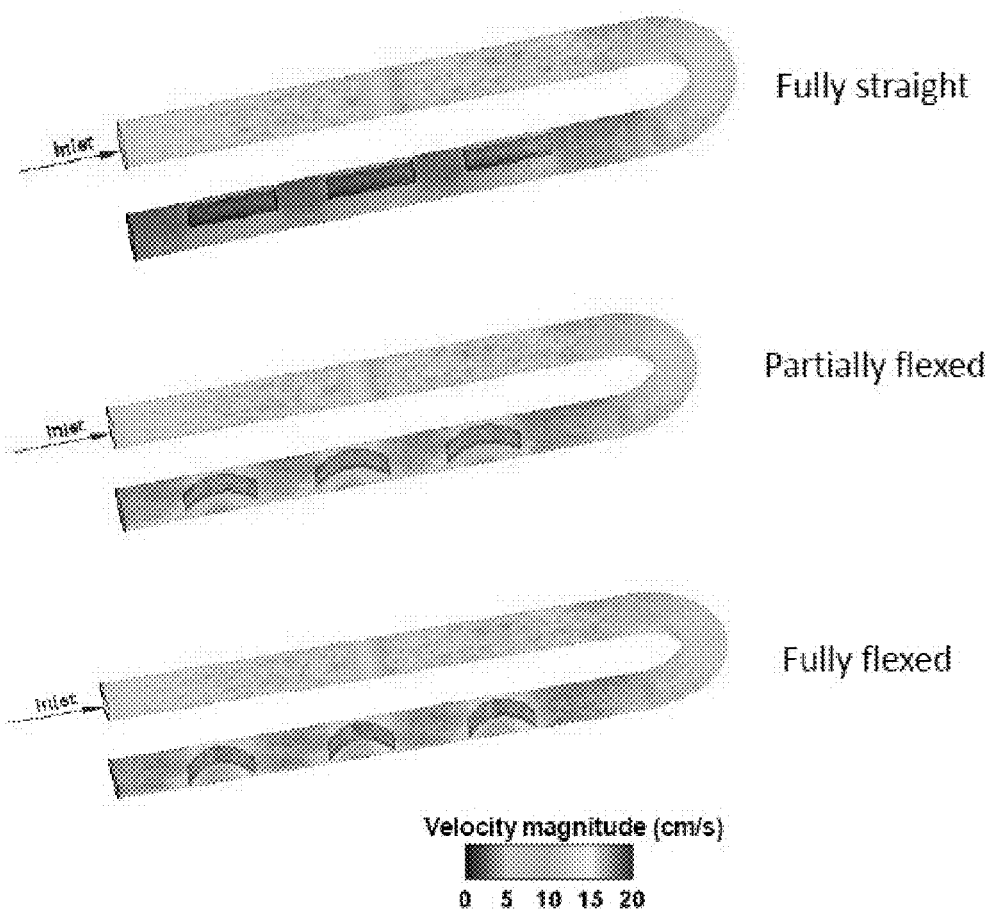
FIG. 5—Uniformity in velocity magnitude contours under various specimen deformation configuration settings. Blood material properties were utilized in the CFD model ($\mu$=3.7 cP, $\rho$=1.04 g/cm$^3$) at Re=486.

Regional shear stress variations were apparent between the outer and inner wall of the specimens (FIGS. 4a and 4b). The average surface shear stresses were computed along its centerline profile for both these regions. The mean±standard deviation (n=3 specimens) along the outer wall was i=29.6±0.68 dynes/cm$^2$ whereas on the inner wall, it was τ=7.56±0.10 dynes/cm$^2$. The small standard deviations among the 3 specimens were indicative of the uniformity in the shear stresses between them. This was largely due to the uniform velocity field (FIGS. 4a and 4b) surrounding the specimens. Notably on the inner wall, the shear stress magnitudes were considerably lower (average τ smaller by ~74% from the centerline profile) in comparison to the outer wall. In addition, a high degree of flow reversal was found to occur on the inner specimen wall.

Figure 7:
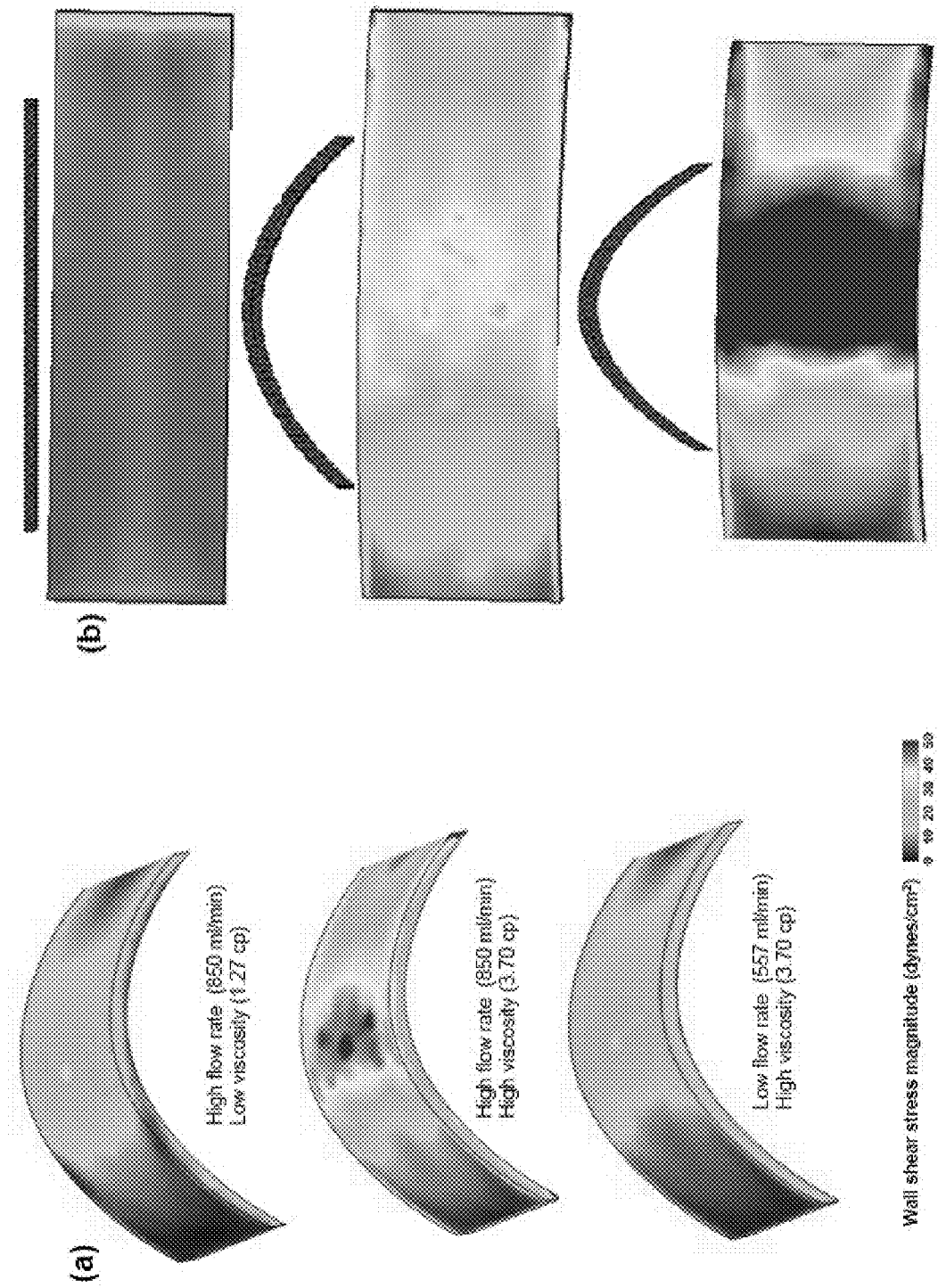
FIG. 7—Sensitivity of shear stress distribution with respect to the relative conditions of: (a) high flow rate (850 ml/min) and low viscosity (regular cell culture media ~1.27 cP), high flow rate (850 ml/min) and high viscosity (Xanthan Gum-augmented media ~3.7 cP) and low flow rate (557 ml/min) and high viscosity (Xanthan Gum-augmented media ~3.7 cP). Resulting Re numbers and mean shear stresses were: [1100, 8.9 dynes/cm$^2$], [390, 17.8 dynes/cm$^2$] and [256, 10.2 dynes/cm$^2$] respectively. b) Outer wall surface shear stress distributions as a function of fully straight (t=0 ms; mean shear stress ~10 dynes/cm$^2$), slightly bent (t=50 ms; mean shear stress ~21 dynes/cm2) and fully bent (t=500 ms; mean shear stress ~24 dynes/cm$^2$) specimen configurations. Blood material properties were used in part b), i.e. ($\mu$=3.7 cP, $\rho$=1.04 g/cm$^3$) at Re=486.

The effect of increasing media viscosity or flow rate alone on fluid-induced surface shear stress distribution indicated that the mean shear stress magnitudes could be doubled using cell culture media that possesses nearly 3 times the viscosity (FIGS. 7A and 7B). Alternatively, the mean shear stresses increased by ~75% when the flow rate was increased by 1.5 times (FIGS. 7A and 7B). Therefore, sufficient dynamic shear stress range under laminar flow conditions was possible in the FSF bioreactor by appropriately selecting viscosity and flow rate parameters.

Figure 8:
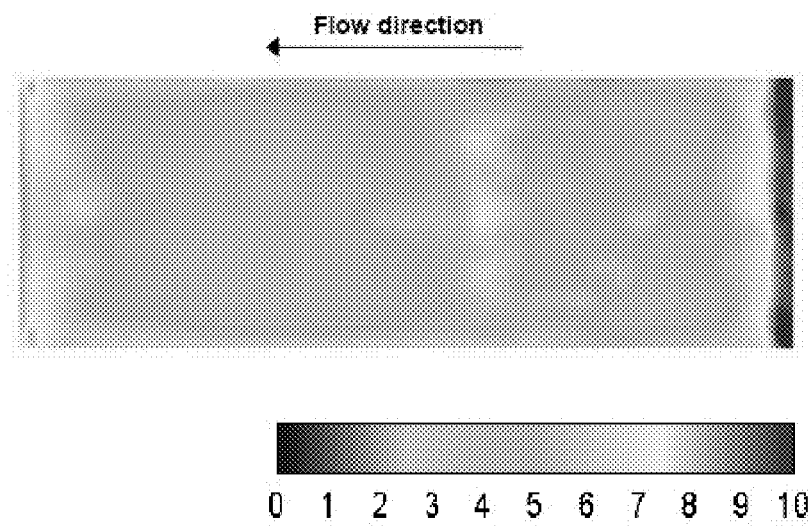
FIG. 8—Fluid-induced surface shear stress distribution on the surface of straight FSF bioreactor specimens using regular cell culture media ($\mu$=1.27 cP, $\rho$=1.01 g/cm$^3$), at Re=1100 and a flow rate of 850 ml/min. The specimen mean shear stress was found to be in the order of 5.1 dynes/cm$^2$, comparable to physiological levels (5-6 dynes/cm$^2$) experienced by native aortic valve leaflets (Sacks, M. S. et al. Philos Trans R Soc Lond B Biol Sci, 2007. 362(1484): p. 1369-91).

The magnitude of fluid-induced shear stresses increased with increased flex states (FIG. 7B), mean values ranging from 10 to 24 dyne/cm2. These values were well within the physiological range of fluid stresses that native heart valves are reported to be subjected to (3-80 dynes/cm$^2$) (Weston, M. W., et al. Ann Biomed Eng, 1999. 27(4): p. 572-9). Yet, if higher values than this are necessary, either the fluid viscosity and/or flow rate could be accordingly, further increased while still maintaining a laminar flow regime. We note however that for heart valves that typical fluid-induced surface shear stress is in the order of 5-6 dynes/cm$^2$ (Sacks, M. S. et al. Philos Trans R Soc Lond B Biol Sci, 2007. 362(1484): p. 1369-91); values within this range were found to be readily obtainable in the FSF bioreactor housing fully straight specimens immersed in standard cell culture media, without the need for viscosity augmenting additives (FIG. 8).

Gas Exchange

Figure 9A:
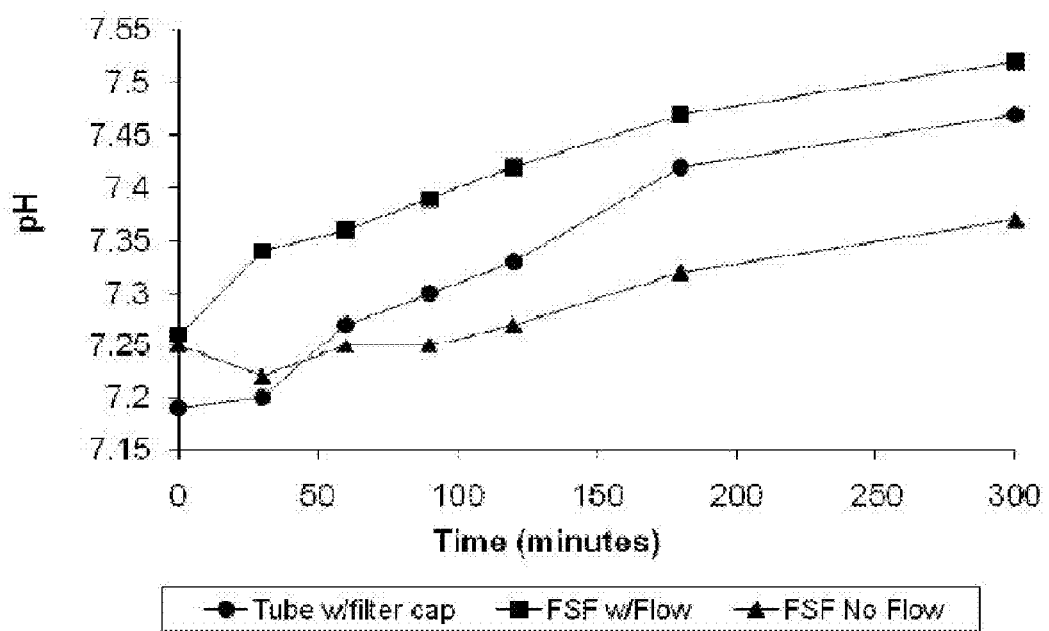
Figure 9B:
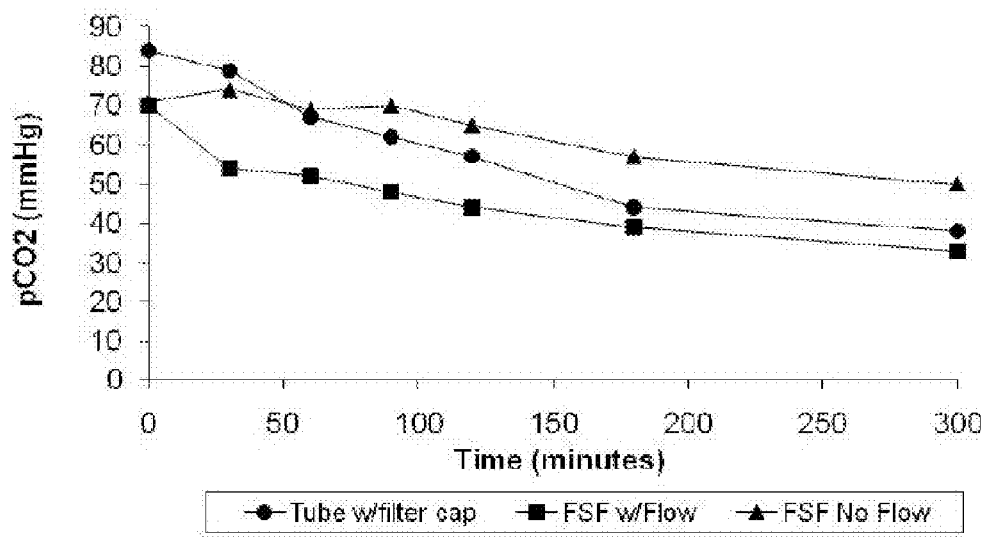
Figure 9C:
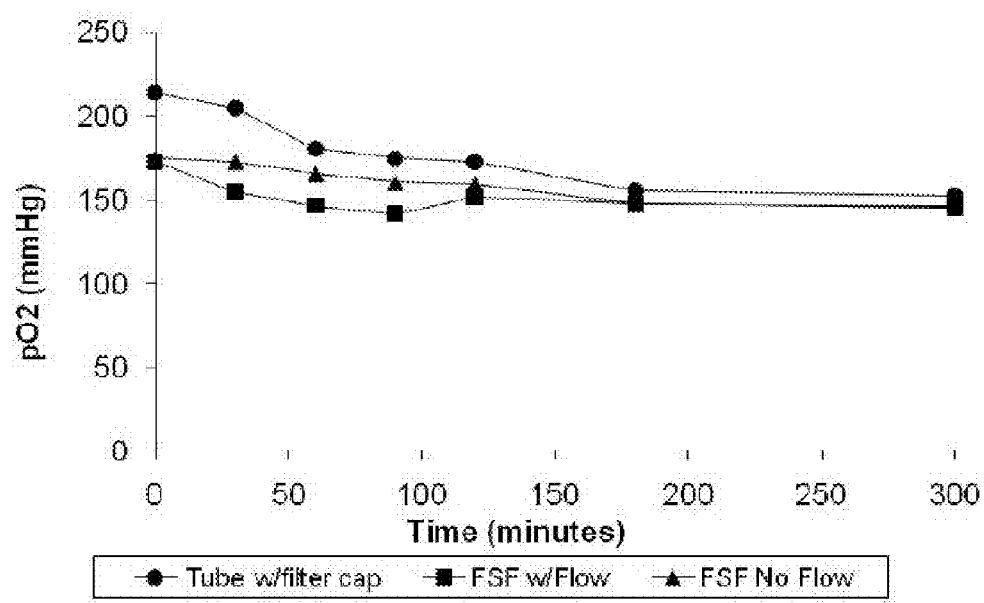

Over a 5 hour period, pH of the media marginally increased (FIG. 9A) while slight decreases in the partial pressure of incubator ambient gases were observed (FIGS. 9B and 9C). At the end of 3 days, no statistical significance (p>0.05) was found in any of the measurements (Table 1) between media contained in the plastic tube with a filtered cap and in the FSF bioreactor when the pump was operational. However without the benefit of flow, only the pO$_2$ levels were found to be insignificant (P>0.05) in comparison to the control group; on the other hand, differences in the mean pH and pCO$_2$ were significant (P<0.05), suggesting that flow in the conditioning chamber is essential to ensuring adequate gas exchange.

TABLE 1

Gas and pH measurements (n = 3 samples/group) taken from the FSF bioreactor after 3 days of incubation.

| Group name | pH | pCO2 (mmHg) | pO2 (mmHg) |
| --- | --- | --- | --- |
| Tube w/filter cap | 7.67 ± 0.04 | 23.3 ± 2.52 | 148 + 3.61 |
| FSF w/flow | 7.63 ± 0.01 | 25.3 ± 0.58 | 147 ± 1.73 |
| FSF no flow | 7.57 ± 0.02 | 29.0 ± 1.73 | 144 ± 2.31 |

Values = mean ± SD.

Sterility Tests

Figure 10:
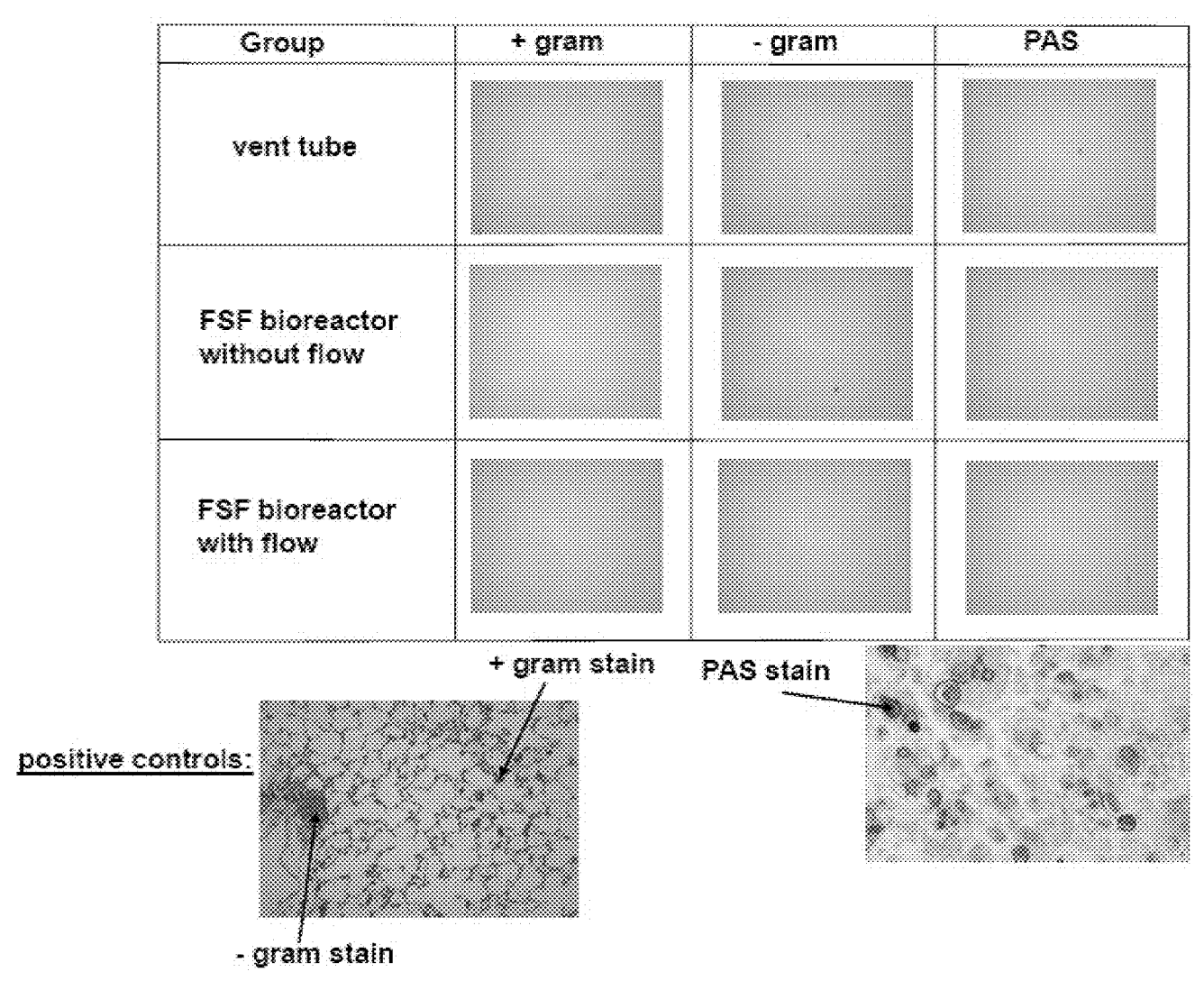

Absence of common bacterial and fungal contamination was verified by histology in media that circulated in the FSF bioreactor for a 5 day period (FIG. 10). Positive and negative gram staining as well as the PAS light green (Carson, F., Histotechnology: A Self Instruction Text. 3rd ed. 2007, Hong Kong: ASCP Press) all stained absent for microbial activity. This result provided some confidence that the FSF bioreactor system could be kept sterile when used for live cell and tissue culture experiments.

Discussion

Need for Physiologic Flow Conditions.

Studies of the development of engineering heart valve tissues studies are relatively more recent than other applications such as skin, blood vessels and cartilage (Sacks, M. S., et al. Bioengineering Challenges for Heart Valve Tissue Engineering. Annual Review of Biomedical Engineering, 2009; Hoerstrup, S. P., et al. Functional living trileaflet heart valves grown In vitro. Circulation, 2000. 102(19 Suppl 3): p. 11144-9; Vesely, I., Heart Valve Tissue Engineering. Circulation Research, 2005. 97: p. 743-755; Syedain, Z. H. et al. Controlled cyclic stretch bioreactor for tissue engineered heart valves. Biomaterials, 2009. 30(25): p. 4078-84; Schmidt, D. et al. Tissue engineered heart valves based on human cells. Swiss Med Wkly, 2006. 136(39-40): p. 618-23; Schmidt, D., et al. In vitro heart valve tissue engineering. Methods Mol Med, 2007. 140: p. 319-30; Robinson, P. S., et al. Functional tissue-engineered valves from cell-remodeled fibrin with commissural alignment of cell-produced collagen. Tissue Eng Part A, 2008. 14(1): p. 83-95; Mol, A., et al. Autologous human tissue-engineered heart valves: prospects for systemic application. Circulation, 2006. 114(1 Suppl): p. I152-8; Mol, A., et al. Tissue engineering of human heart valve leaflets: a novel bioreactor for a strain-based conditioning approach. Ann Biomed Eng, 2005. 33(12): p. 1778-88; Hoerstrup, S. P., et al. Tissue engineering of functional trileaflet heart valves from human marrow stromal cells. Circulation, 2002. 106(12 Suppl 1): p. I143-50; and Sutherland, F. W., et al. From stem cells to viable autologous semilunar heart valve. Circulation, 2005. 111(21): p. 2783-91). A common theme is the notion of simulating tissue formation in a physiological environment. Recent engineered heart valve tissue studies involving pulmonary pressure (20 mmHg mean value) and pulsatile flow environments in our laboratory demonstrated enhanced collagen production/cell by ~35% over cyclically flexed specimens subjected to concomitant sub-physiologic shear stresses (Ramaswamy, et al. 2010 February; 31(6):1114-25). Indeed, it has been shown that in the context of TEHVs, that appropriate mechanical stimulation of the constructs is advantageous to its development, specifically, that exposure to mechanical stress states in vitro improves tissue production, organization, and function (Mendelson, K. a. S., F. J., Heart Valve Tissue Engineering: Concepts, Approaches, Progress, and Challenges. Annals of Biomedical Engineering, 2006. 34(12): p. 1799-1819). However, since optimal mechanical conditioning regimens essential to the overall success of the implant are still largely unknown, there is still an unmet need to develop bioreactors that can provide an avenue to delineate the effects of different stress states on engineered tissue formation.

Although due consideration to the importance of physiological levels of fluid-induced shear stress magnitudes has been considered (Sucosky, P., et al. Design of an ex vivo culture system to investigate the effects of shear stress on cardiovascular tissue. J Biomech Eng, 2008. 130(3): p. 035001), this was done without flexural and/or stretch components. In fact, few bioreactors (Cacou, C., D. et al. A system for monitoring the response of uniaxial strain on cell seeded collagen gels. Med Eng Phys, 2000. 22(5): p. 327-33; Jockenhoevel, S., et al. Cardiovascular tissue engineering: a new laminar flow chamber for in vitro improvement of mechanical tissue properties. Asaio J, 2002. 48(1): p. 8-11; Kim, B. S. et al. Scaffolds for engineering smooth muscle under cyclic mechanical strain conditions. J Biomech Eng, 2000. 122(3): p. 210-5; and Mitchell, S. B., et al. A device to apply user-specified strains to biomaterials in culture. IEEE Trans Biomed Eng, 2001. 48(2): p. 268-73) have to date focused on individual mechanistic effects of external stimuli on engineered cardiovascular tissue formation. Cyclic flexure, stretch and flow stresses are present during native valve leaflet deformation and have specifically exhibited both individual and coupled stimulatory effects, and are thus important for systemic evaluation of their effects on different scaffold materials and cell sources.

Previously, we developed a bioreactor permitting coupled or decoupled flow, stretch, and flexure on several rectangular strips of tissue (Engelmayr, G. C., Jr., et al. Ann Biomed Eng, 2008. 36(5): p. 700-12). Subsequent studies demonstrated enhanced tissue formation under combined cyclic flexure and flow stress states (Engelmayr, G. C., Jr., et al. Biomaterials, 2006. 27(36): p. 6083-95), but the fluid-induced stresses were found to be relatively very low (less than 2 dynes/cm$^2$). Our recent findings (Ramaswamy, et al. 2010 February; 31(6): 1114-25) suggest that fluid-induced stresses play a dominant role in tissue formation rates and scaling the conditioning to physiological scales may have added benefits. In addition, specific flow distributions that induce regionally unique flow patterns such as oscillatory flow may also play a critical role depending on the cell sources that are used, such as bone marrow derived stem cells (Id.; Arnsdorf, E. J., et al. Non-canonical Wnt signaling and N-cadherin related beta-catenin signaling play a role in mechanically induced osteogenic cell fate. PLoS ONE, 2009. 4(4): p. e5388; Arnsdorf, E. J., et al. Mechanically induced osteogenic differentiation—the role of RhoA, ROCKII and cytoskeletal dynamics. J Cell Sci, 2009 122(Pt 4): p. 546-53; and Li, Y. J., et al. Oscillatory fluid flow affects human marrow stromal cell proliferation and differentiation. J Orthop Res, 2004. 22(6): p. 1283-9). Given the complexities of cellular response to biophysical stimuli and subsequent tissue formation, these results underscore the significant need for specialized systems that combine the major heart valve deformation/loading modes (flow, stretch and flexure) at physiological levels.

Unique Bioreactor Design Features

Figure 6:
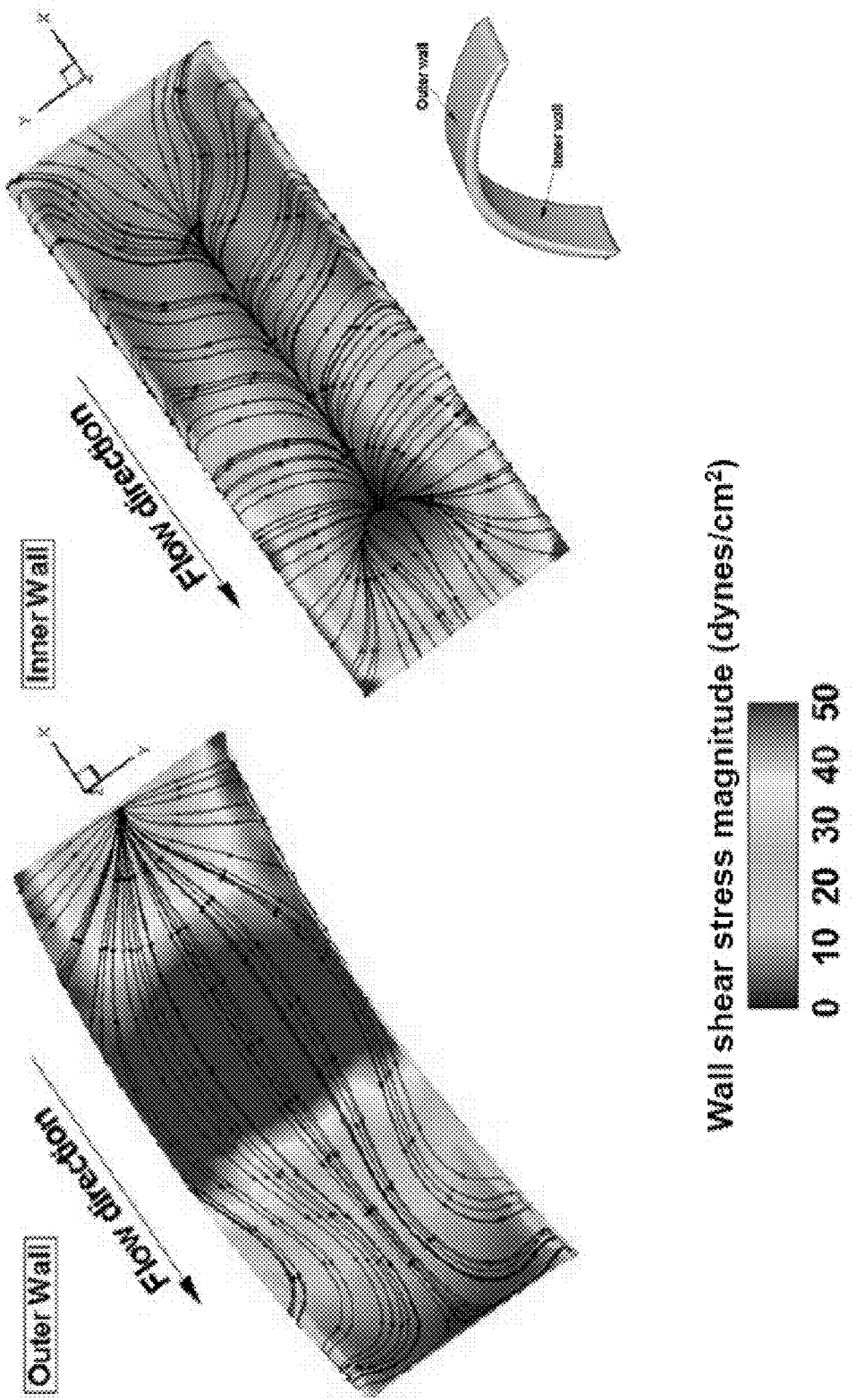
FIG. 6—Regional shear stress distributions on the inner and outer specimen walls. Note the larger shear stress magnitudes on the outer specimen wall making it analogous to the ventricular side of the valve leaflets. Note also the large degree of flow reversal on the inner wall which is known to occur on aortic side of heart valves (Sacks, M. S. et al. Heart valve function: a biomechanical perspective. Philos Trans R Soc Lond B Biol Sci, 2007. 362(1484): p. 1369-91). The inner wall of the FSF-bioreactor specimen is thus analogous to the aortic or pulmonary side of the valve leaflets ($\mu$=3.7 cP, $\rho$=1.04 g/cm$^3$) at Re=486.

The primary novel component of the device consists of a narrow, cylindrical flow chamber that contains a flow field that is generated by a peristaltic pump. Most importantly, the device's conditioning chamber geometry permits exertion of physiologically relevant surface fluid shear stresses (5-6 dynes/cm$^2$) (Sacks, M. S. et al. Philos Trans R Soc Lond B Biol Sci, 2007. 362(1484): p. 1369-91) on tissue specimens while at the same time, preserving laminar flow. The laminar flow requirement is important from a biomimetic standpoint since blood flow in arteries is laminar in most cases. It is also worthwhile noting that the shear stress patterns on the inner and outer walls of the bioreactor specimens were analogous to the aortic and ventricular sides of the aortic valve (Id.), given that much lower magnitudes of shear stresses and larger degrees of flow reversal were present on the surface of the inner wall compared to the outer wall (FIG. 6). Such variations that mimic the native valve shear stress spatial distribution may serve useful in detailed evaluation of specific fluid-induced mechanistic effects on regional tissue development.

The bioreactor was built out of an amorphous thermoplastic polyetherimide material (ULTEM) mainly because ULTEM is non-toxic and very resilient to ethylene oxide and autoclave sterilization procedures; this was confirmed by exposure of the device to several cycles in an ethylene oxide gas sterilizer, which did not cause any material deterioration or loss of functionality. Flow could be diverted using stopcocks in the system to pump media out of and into the bioreactor and these media changes were possible without the removal of the device from the incubator, thereby minimizing exposure to non-sterile environments. Sterility studies examining media circulating through the bioreactor for 5 days revealed no signs of microbial contamination. When the pump is in operation, adequate gas exchange within the main bioreactor chamber was verified.

The bioreactor which accommodates up to 12 specimens readily fits into a standard sized incubator. There are 4 chambers (3 specimens/chamber) each of which can be simultaneously subjected to a unique conditioning protocol (e.g. flow alone, flexure alone, flexure and flow, no flow and no flexure). A linear actuator connected to the specimens provided cyclic flexure and stretch capabilities. The excellent MRI susceptibility matching properties of ULTEM to water combined with the ability to easily replace specific components (screws, actuator rods, etc) of the device with plastic and titanium equivalents made the bioreactor adaptable for use in an MRI instrument. We were able to previously demonstrate (Ramaswamy, et al. 2010 February; 31(6):1114-25) that specimens inside the chamber could be successfully imaged by MRI.

Although the results herein focus on steady flow conditions, we note that the pump could be programmed to generate pulsatile flow waveforms if necessary. Other novel design features, such as the removable tissue housing and ring coupling system allowed for the implementation of such a device configuration. A detachable sample holder was devised for ease of sample incorporation and to maintain a workable small diameter environment. An adequate dynamic range of flow rates was made possible by integrating the FSF bioreactor with a commercially available peristaltic pump through which either steady or pulsatile flow are permissible. In addition, the pump's powerful electric motor would enable more viscous liquids to be efficiently driven through the system. Thus, from a practical viewpoint, the exertion of higher mean fluid-induced surface shear stresses on housed specimens would be achievable using this bioreactor system by appropriately selecting the flow rate, the fluid viscosity and the sample configuration, for example the level of flexure in the specimens. We note that if the media is non-Newtonian in nature, that shear thinning effects (the extent to which will depend on the flow rate chosen) may come into effect and care should be taken to establish the actual media viscosity (and hence shear stresses of the housed specimens). From the flow simulations reported in this study, it is apparent that in the context of physiological conditioning of engineered heart valve tissues, that the use of regular cell culture media (mean shear stress in a fully flexed specimen ~8.6 dynes/cm$^2$; fully straight specimen ~5.1 dynes/cm$^2$) without the need for viscosity increasing additives, is acceptable.

Conclusions

We presented a novel bioreactor design that was built for standard incubator housing and successfully tested for gas exchange and sterility for the study of engineered heart valve leaflet tissue formation. An actuator can flex or stretch up to 12 specimens with or without flow and thus, mechanistically provides an analogous system to tri-leaflet valves which serves as a testbed for TEHV conditioning protocol optimization. The device focuses on the fluid mechanic advantages inherent to narrow, cylindrical, curved tube geometries that permit a large dynamic range (0-24 dynes/cm$^2$) of fluid-induced shear stress magnitudes to be imparted onto the surface of the housed specimens while retaining a laminar flow regime. The range predicted exceeds what we believe to be a plausible limit to the maximum value of physiologically relevant shear stress magnitudes necessary for TEHV studies. However if needed, further increases in the surface shear stresses are possible since the electrically driven pump connected to the bioreactor can efficiently drive greater viscosity liquids. Augmentation of the media with biologically safe additives can be performed to increase its viscosity. The design of the tissue deformation modes (flexure and stretch) in combination with physiological levels of shear stress make it an indispensible tool for mechanistic studies on evolving tissue engineered constructs.

Example 2

The following, published in Ramaswamy, et al. 2010 February; 31(6):1114-25, is an example of how the bioreactors described herein might be used, but using a different bioreactor design. The following study was conducted to determine if the extracellular matrix (ECM) growth patterns observed in previous CFF studies could be duplicated in a functional tri-leaflet valve. Specifically, we utilized ovine MSCs to seed nonwoven PGA/PLLA fabrics and imposed pulmonary artery conditions on intact tri-leaflet valve constructs and compared them to valves grown under static tissue culture conditions. The resulting formed tissues were studied using histological and biochemical measures. In addition, it has been shown that media containing ascorbic acid-2-phosphate (AA2P) and basic fibroblast growth factor (bFGF) augmented tissue formation. Owing to the critical role of collagen in the functional requirements of engineered heart valve tissues, we assessed the coupled effects of ascorbic acid 2-phosphate (AA2P) and basic fibroblast growth factor (bFGF) on collagen and GAG formation. Next we combined these biochemical enhancements with physiological conditioning on tri-leaflet heart valve constructs to evaluate our ability to perform scale-up at the organ level. Finally, in an effort to gain insight into the potential stimulatory mechanisms of MSC seeded TEVC tissue formation, we developed detailed computational fluid dynamic (CFD) models of the CFF bioreactor specimens to specifically delineate the nature in which fluid-induced shear stresses act CFF specimens, and related them to similar patterns reported for the native tri-leaflet valve.

Methods

Isolation and Characterization of MSCs

In brief, 10 ml/kg of whole bone marrow was aspirated from the iliac crest of neonatal sheep. Cells were centrifuged on a Ficoll gradient in order to obtain the mononuclear cell fraction. Red blood cells were lysed with ammonium chloride, and the remaining mononuclear fraction was plated onto bacteriologic plates. Medium was initially changed after 48 h, and adherent cells were passaged.

MSC characterization was performed as follows. Briefly, a sub-population of these cells were grown and plated at 10,000 cells/cm$^2$, and after initial culture in standard medium, cells were grown in media known to differentiate MSCs into fat cells (adipogenic medium), bone cells (osteogenic medium) or cartilage (chondrogenic medium). After three weeks, cells were found to differentiate into the three cell types. Subsequently, characterized MSCs were cryopreserved in culture medium supplemented with 5% dimethyl sulfoxide (DMSO) and were shipped on dry ice.

MSC Culture and AA2P and bFGF Supplementation Studies

MSCs were expanded in Dulbecco's modified Eagle's medium (DMEM) supplemented with 10% fetal bovine serum, 1% antibiotic-antimycotic plus HEPES buffer (all purchased from Invitrogen, Carlsbad, Calif.). Cells were at passage 8-10 when sufficient numbers were available for scaffold seeding. A needled nonwoven scaffold consisting of 50:50 blend of PGA and PLLA fibers (Concordia Fibers, Coventry, R.I.) was utilized as the scaffold for all experiments. The PGA/PLLA scaffolds had an initial fabric thickness of 1.53 mm and density of 59.8 mg/ml. Scaffolds were cut into 5 mm diameter disks with a biopsy punch (Acuderm, Inc., Fort Lauderdale, Fla.) and cold gas sterilized with ethylene oxide prior to seeding. One scaffold was placed into each of 12 seeding tubes. Each seeding tube consisted of a 50 cc centrifuge tube (Product #91050; TPP, Trasadingen, Switzerland) fitted with a vent filter cap from a 50 cc tissue culture tube (Product #91253; TPP), thereby allowing for gas exchange during seeding. Seeding solution (12 ml) was added to each tube to yield a seeding density of ~17×10$^6$ cells/cm$^2$. The tubes were rotated at 8 rpm (Labquake rotisserie rotator, Barnstead-Thermolyne, Dubuque, Iowa) inside an incubator operating at 37° C. and 5% $CO_2$ for 30 h, with the medium was changed every 6 h.

Following 30 h seeding, each MSC-seeded scaffold was moved to an individual well of a 6-well dish (Costar Ultra Low Attachment; Corning, Inc, Corning, N.Y.) and maintained in static culture for 3 or 6 weeks prior to analysis (n=6 specimens/group/time point). For the control group, basal culture medium used for culturing the MSCs was maintained. For the bFGF/AA2P group, the basal medium was supplemented with 2 ng/mL (Peprotech, Inc., Rocky Hill, N.J.) of bFGF, consistent with previously utilized amounts and 82 μg/mL of AA2P (Sigma, St. Louis, Mo.). Note that the concentration (w/v) of AA2P was chosen to maintain the same molar concentration of a typically used 50 μg/mL concentration for L-ascorbic acid (i.e., 0.28 mM), accounting for the higher molecular weight of AA2P versus L-ascorbic acid (289.54 (anhydrous basis) versus 176.12 g/mol)

Construct Fabrication and Seeding

PGA/PLLA nonwoven scaffolds were cut into a leaflet shape with the three leaflets (total surface area=22.3 cm$^2$ surface area, total volume=3.41 cm$^3$) sewn onto a plastic frame to form the tissue engineered valve construct (TEVC). Each TEVC was placed in a hybridization tube (Fisher Scientific, Pittsburgh, Pa.) and subjected to Ethylene Oxide gas sterilization for 16 h. A seeding solution netting 6×10$^6$ cells/cm$^2$ was introduced to each TEVC, with the seeding solution and tissue culturing medium identical to the culturing media utilized in the bFGF/AA2P supplementation studies. Hybridization tubes were subsequently placed on a rotisserie (Fisher Scientific). The tubes were rotated at 8 rpm inside a standard cell culture incubator operating at 37° C. and 5% $CO_2$. During the first week following scaffold seeding, the spent media was centrifuged to salvage as many cells still unattached to the leaflets and the cell pellet was added to fresh media. Media changes were done daily during this first week, with the size of the cell pellet negligible after this period. Media changes beyond the first week were performed twice weekly.

Dynamic Conditioning

Dynamic conditioning was performed through the use of an organ-level heart valve bioreactor described in (Hildebrand D K, et al. Design and hydrodynamic evaluation of a novel pulsatile bioreactor for biologically active heart valves. Ann Biomed Eng 2004; 32(8):1039-49). In brief, this device consists of a vented atrium which passively fills a pneumatically driven ventricle with a mechanical inflow valve. This device has the ability to regulate pressure and pulsatile flow conditions. After scaffold cell seeding, the TEVC was mounted onto the threaded stent holder in the bioreactor system. Flow rate in the bioreactor was measured using an ultrasonic flow sensor and flowmeter system (Transonic Systems Inc., Ithaca, N.Y.) and was maintained at an average of 1.15 LPM. Peak and mean fluid pressure across the valve were set to 45 mmHg and 20 mmHg to simulate normal pulmonary artery pressure conditions. A pulse rate (analogous to heart rate) of 60 beats/min was prescribed. Total media volume in the bioreactor was maintained at approximately 2.5 LPM with media changes on average being performed once weekly.

The overall study design for dynamic and static groups is summarized in Table 2. All valves cultured underwent static (i.e., no mechanical conditioning) rotisserie culture for a period of 3 weeks and a total of 6 leaflets were terminated at the 3 week timeframe. Another 12 leaflets were allowed to continue developing for a total culture period of 6 weeks, in which 6 were subjected to static culture conditions and 6 to dynamic culture conditions.

TABLE 2

Summary of endpoints in organ-level TEPV experiments.

| GROUP # | Endpoint | Total leaflets (N) (one-side surface area of a leaflet ~7.4 cm$^2$) | BMSC Seeding density (cells/cm$^2$) | Leaflets utilized for collagen/GAG/DNA assays | Leaflets utilized for Histology |
|---|---|---|---|---|---|
| Group 1 | 3 week static, rotisserie culture | 6 leaflets | 6 × 10$^6$ | 5 | 1 |
| Group 2 | 6-week static, rotisserie culture | 6 leaflet | 6 × 10$^6$ | 5 | 1 |
| Group 3 | 3-week static followed by 3-week dynamic pulmonary artery pressure conditioning (Peak pressure = 45 mmHg, Mean pressure = 20 mmHg) | 6 leaflets | 6 × 10$^6$ | 5 | 1 |

Histological Assessment

Histology for bFGF/AA2P supplementation studies was performed. In brief, a thin sample of each MSC-seeded scaffold (~25×1×1 mm) was fixed in 10% formalin and embedded in paraffin. Serial sections (6 mm) from 3-week old samples were stained with hematoxylin and eosin (H&E) for morphology and from 6-week old samples with rabbit polyclonal anti-human primary antibodies against collagen I (1:100; AB292, Abcam, Cambridge, Mass.), and collagen III (1:200; AB778, Abcam). Immunostaining was performed by the Avidin-Biotin-peroxidase-Complex (ABC) method with biotinylated goat anti-rabbit secondary antibodies (Vector Laboratories, Burlingame, Calif.) and using 3-amino-9-ethyl carbazole (Dako Corporation, Carpinteria, Calif.) as a substrate. Sections were counterstained with Gill's hematoxylin solution (Sigma).

For specificity controls, an appropriate nonimmune IgG was substituted for the primary antibody. TEPV leaflets were subjected to histological evaluation for collagen as a precursor to detailed biochemical analysis. Leaflets was fixed in 10% formalin and embedded in paraffin. Serial sections (6 mm) were prepared and subsequently stained with picro sirius red for qualitative assessment of collagen alignment using polarized light microscopy.

DNA and Biochemical Assays

Specimens from the basal culture and bFGF/AA2P treated medium groups were removed following 3 (n=6/group) and 6 (n=6/group) weeks and subjected to DNA and collagen biochemical assays. In addition, 5 leaflets in each of the 3 organ-level TEPV categories (3-week static, 6-week static and dynamic) were cut into smaller parts (between 5 and 10 pieces/leaflet) and weighed. DNA, sulfated glycosaminoglycans (S-GAG) and collagen were quantified. For DNA content, each specimen was digested with a buffered 0.125 mg/ml papain solution for 10 h in a 60° C. water bath. The extracts were then assayed using the PicoGreen dsDNA quantitation kit (Molecular Probes, Eugene, Oreg.) per the manufacturer's instructions and using the blue channel of a TBS-380 Mini-Fluorometer (Turner Biosystems, Sunnyvale, Calif.). A portion of extract from the papain digest was reserved for the S-GAG assay which was performed according to the guidelines provided with the Blyscan™ assay kit (Biocolor Ltd., Newtownabbey, N. Ireland) using a Genesys 20 spectrophotometer (Thermo Spectronic, Rochester, N.Y.) set to an absorbance of 656 nm.

For collagen, samples were digested with a solution of 0.5 M acetic acid (Sigma) and pepsin (1 mg/ml Pepsin A (P-7000); Sigma). Digestions were carried out overnight (w16 h) on a rocker (Orbitron Rotator™; Boekel Scientific, Feasterville, Pa.) at 4° C. Collagen extracts were then assayed according to the guidelines provided with the Sircol™ assay kit (Biocolor Ltd.) using the same spectrophotometer used in the S-GAG assay (Thermo Spectronic) set to an absorbance of 540 nm.

Mechanical Evaluation

While our optical system was capable of imaging the TEVC leaflets directly, the use of the phenol red in the media (necessary for verifying any pH changes) limited our ability to visualize the leaflet surfaces directly. While use of non-dye media was considered, the novelty of the present study made it necessary to use the dye in all experiments to verify cell viability and if bacterial contamination occurred. However, we have shown that a polyacrylamide gel can simulate effective tissue properties (under the assumption of tissue mechanical isotropy) in PGA/PLLA scaffold-gel composite scaffolds.

Hence, in the present study an equivalent scaffold-only TEVC control was prepared for imaging, and an agarose gel (AG) applied onto the leaflet scaffolds to simulate the presence of tissue for mechanical characterization and subsequent visualization. Specifically, the AG was prepared by dissolving agarose powder (Type VII, low gelling temperature, Sigma) in phosphate buffered saline (Invitrogen) at the desired concentration to produce a 6% weight per unit volume mixture. The mixture was then heated to 85° C. to allow complete dissolution and poured onto a tri-leaflet TEPV construct. The construct was then allowed to cool at 4_C for 15 min. The 6% AG used provided an equilibrium aggregate modulus of 138 kPa, and the construct has an effective stiffness (E) of w1000 kPa at this gel modulus. Gel and scaffold-only TEPVs were mounted into the organ-level bioreactor and subjected to a peak static pressure of 20 mmHg to simulate full diastolic loading.

To ensure that our TEVC leaflet analogs mechanically behaved in a manner similar to engineered heart valve tissue, stiffness properties of the former were directly measured. AG-leaflets (with 6% agarose gels) and scaffold only specimens were mechanically tested in the preferred direction of fibers within the scaffold. A device capable of imposing three-point bending on tissue was employed to characterize the flexural stiffness of the scaffold-only and scaffold-gel composites. Both negative and positive curvature directions (n=6 measurements, 3 in each direction) were imposed on samples during testing.

Leaflet Surface Reconstruction

A design goal of the TEVC used in this study was to approximate a semi-cylindrical geometry to maintain geometric similarities to the cylindrical shape of fully bent, rectangular CFF bioreactor specimens. While not a intended to be an exact match, we sought to maintain as an overall geometric similarity. To verify this leaflet geometry, 3D reconstructions of the leaflet surface were carried to determine the shape of the AG-leaflets. In brief, a 14 mW diode laser module with an interchangeable optical pattern generator head (Lasiris Inc., Canada) was used to project a matrix of 19×19 dots on to the leaflet surface. A custom-built index-matching chamber housing the TEPV stent was filled with 60:40 water:glycerin solution for refractive index matching purposes. The loop of the organ-level bioreactor was also filled (~2.5 L) with the same water-glycerin solution.

Image acquisition was performed through the use of two cameras (Basler, A504k, Sydney, Australia), with image capture and subsequent acquisition for each camera occurred simultaneously for the two views and was initiated and controlled using commercially available image capture software (Advanced Digital Vision Inc, Natick, Mass.). Captured images were analyzed using SigmaScan image processing software (Systat Software Inc., Chicago, Ill.). The images were first processed to enhance contrast; then the location of each laser dot in each image was recorded as the centroid of the laser dot. Corresponding laser dot locations in each view were identified, and a calibrated standard discrete linear transform (DLT) was used to convert these pixel locations into three-dimensional (3-D) spatial coordinates. Leaflet, 3-D surface meshes (using triangular elements) were created from the 3-D points using Gambit (Fluent, Lebanon, N.H.) meshing software.

Computational Fluid Dynamic (CFD) Analysis

To gain a more detailed information of the surface flow and shear stress patterns acting on the CFF specimens under increasing flexure states, we conducted the following quasi-static analysis. Details on the discretization of the sample geometry at each new position have been presented previously (Ramaswamy S, et al. Effects on Specimen Motion on Flow Induced Shear Stresses in Engineered Heart Valve Tissues. In: 8th World Biomaterials Congress: Crossing Frontiers in Biomaterials and Regenerative Medicine; 2008 May 28-Jun. 1 Amsterdam, The Netherlands; 2008). In brief, we assumed that the flexure of rectangular scaffold strips in the CFF bioreactor followed a parabolic profile. The bent configuration of the samples was determined numerically based on the rate of specimen displacement. Additionally we assumed that the sample along its length (x-direction) conformed to the equation of an arc length with the constraint of a fixed length (L) at any time point of 25 mm, given by:

$$\int_a^b \sqrt{1+(2Cx)^2}\, dx = L \quad (1)$$

where a is the position of the stationary post attachment to a CFF bioreactor specimen, b is the new position of the moving post attachment to the specimen, as it moves towards the stationary post (determined from the prescribed actuator motion) and C is the constant that changes according the new position b. The new configuration of the sample due to bending was hence computed (Mathcad v.14 PTC, Needham, Mass.).

A laminar flow, quasi-static CFD simulation was performed using commercially available software (Fluent, Ansys Inc, Lebanon, N.H.). 11 different time points in a cycle of 0.5 Hz were simulated, wherein CFF bioreactor specimens initiated from a fully straight configuration to increasing levels of flexure. A structured grid consisting of 1.43 million hexahedral elements (1.54 million nodes) was constructed (Ansys). The density and viscosity material properties were set to 1010 kg/m$^3$ and 0.00076 kg/m-s consistent with previously utilized values for cell culture media. Convergence criteria for continuity and 3D equations of motion were set to residual values of <10$^{-9}$. A plug flow inlet velocity boundary condition of 5.5 cm/s (equivalent to an operational speed of 2000 RPM for the flow source component of the device) was prescribed and allowed to develop through the addition of an extended entrance length connected to the main configuration of the CFF device. Post-processing (Tecplot 360, Tecplot Inc, Bellevue, Wash.) was performed in order to visualize the shear stresses contours and friction streamlines (shear stresses tangent to the shear stress vector field) on the sample walls.

Data Analysis and Statistics

The CFF bioreactor provided a platform in which the effects of different combination of TEPV variables such as coupled/decoupled CFF stress states, scaffold material(s) and cell sources can be optimized in a straightforward manner. However, a precursor to using the device for this purpose was to first establish if tissue formation at the organ-level was reproducible in rectangular, CFF bioreactor specimens. Thus, linearized rates of collagen production were utilized to compare the effects of bFGF/AA2P inclusion, and organ versus CFF level bioreactor conditioning. In addition, the amount of collagen produced at 6 weeks by combined flow and cyclic flexure in the CFF bioreactor was predicted based on its linear rate over a 3 week period. DNA content in CFF studies was assumed to be the same as the amount determined after 3 weeks of static culture in bFGF/AA2P supplemented media. Justification for this was based on the findings of DNA levels found (see results section) in dynamic and static groups in the organ level studies. Assay results are presented as mean±SEM. Group comparisons were performed using the Student t-test, with statistical significance taken as p<0.05.

Results

Leaflet Shape and Scaffold Mechanical Behavior

The surface reconstruction of a representative leaflet at end diastole (maximum closure phase) demonstrated that the leaflet conformed to a circular cross-section hence, which is the nature of bending that occurs during flexure of straight, rectangular-shaped, CFF-bioreactor specimens. We were thus able to approximately approximate our CFF specimen geometry in the TEVC. In the preferred direction of fibers, a flexural modulus of 161±8 kPa (mean±SEM) was determined for the scaffold-only, consistent with previous findings. A much higher flexural modulus of 940±56 kPa was found for the AG-gel scaffold. This amount were comparable to previously predicted effective stiffness values (e.g., Ey1000 kPa) for TEPV analogs using a polyacrylamide gel suggesting functional equivalence between the two materials. In addition, as a measure of suitability to serve as TEPV analogs, the AG-gel leaflets had a comparable flexural modulus to previously reported values (E=978±228 kPa) for engineered heart valve tissue derived from ovine smooth muscle cells subjected to cyclic flexure conditioning for 3 weeks.

Leaflet Histology

After 3 weeks of culture, H&E staining demonstrated enhanced tissue formation in the bFGF/AA2P group versus the basal media cultured tissue which served as a control group. Specifically, tissue formation appeared to be sparse in the basal media group, with cells and extracellular matrix (ECM) localized primarily near the scaffold perimeter. In contrast, abundant cells and ECM were observed throughout the scaffolds, including the central region, in the bFGF/AA2P group. In addition, immunostaining for collagen I appeared to be enhanced in the bFGF/AA2P group over the controls. Collagen III staining demonstrated a similar pattern of expression. Collagen alignment was observed through histological staining of TEPV sections taken from the 6-week static group. The abundant presence of collagen in the microstructure found after 6 weeks of incubation was consistent with previous studies performed in our laboratory that showed evidence of sparse collagen aggregates after being cultured for half (3 weeks) the culture time.

Biochemical and DNA Assays

Initial DNA content in the basal media and bFGF/AA2P supplemented groups was determined to be ~500 µg DNA/g wet weight. Subsequently, dramatic DNA loss was observed (at 3 weeks: 375±29 µg DNA/g wet weight for basal culture media group and 369±28 µg DNA/g wet weight bFGF/AA2P group; at 6 weeks: 287±17 µg DNA/g wet weight for basal culture media group and 274±47 µg DNA/g wet weight for bFGF/AA2P group). A similar degree of cellularity between the groups for both culture durations (p>0.05, for both 3 and 6 weeks) was found. The progressive loss of cellularity following MSC seeding is similar to previous observations that suggested a possible inefficiency in attachment of the MSCs to serum proteins adsorbed to the scaffold PGA and PLLA fibers. Consistent with H&E staining, biochemical assays demonstrated AA2P/bFGF stimulated significantly higher collagen concentrations versus basal culture medium (p<0.05, þ 180% at 3 weeks and p<0.05, þ 77% at 6 weeks). As shown in FIG. 4a, the net collagen production/DNA was also found to be significant between the 2 groups (p<0.05, +185% at 3 weeks and p<0.05, +85% at 6 weeks).

Biochemical assays of the TEVC leaflets revealed nearly a 4-fold increase in collagen production when subjected to additional 3-weeks of dynamic conditioning under physiologically relevant pulmonary artery pressure conditions (20/45 mmHg mean/peak pressure). Comparisons of the dynamic conditioning group with collagen levels found in both the 3 and 6 week static groups were found to be statistically significant (p<0.05). No significance (p>0.05) in net collagen production was observed between the 3 and 6 week static groups.

Decreased GAG production was observed over time (p>0.05, dynamic versus 6-week static; p<0.05, 3-week static versus 6-week static or dynamic groups). This decrease in the formation of GAGs was consistent with those observed when flexure and flow conditioning was coupled on CFF bioreactor samples. While a temporal decrease in the net DNA of the TEPV leaflets occurred (p<0.05, 3-week static versus 6-week static groups), dynamically conditioned constructs were able to maintain their level of DNA to their initial levels determined at the end of first three weeks of static culture (p>0.05, 3-week static versus dynamic groups).

Collagen Production on TEVC Leaflets Versus CFF-Bioreactor Specimens

The inclusion of bFGF/AA2P was found to have a ~3-fold increase in collagen production/MSC over basal media alone at 3 weeks of culture. From the 3-6 week period, dynamic mechanical conditioning effects coupled with bFGF/AA2P supplementation on TEPVs resulted in a 33% increase in collagen production/MSC. Our previous studies with the CFF-bioreactor did not include the use of bFGF/AA2P. At 3 weeks, the effect of dynamic conditioning alone in that study resulted in 23% less collagen produced/MSC versus culturing with bFGF/AA2P media supplementation alone.

To allow comparisons of tissue formation at 6 weeks with the CFF-specimens, we first noted that in our bFGF/AA2P studies that no significant differences (p>0.05) of DNA levels were found at 6 weeks between basal media and bFGF/AA2P supplemented groups. In addition, the DNA level was maintained beyond the initial 3 week period when dynamic organ-level conditioning was used suggestive of DNA preservation by conditioning. Hence for comparison with CFF bioreactor conditioned specimens, we assumed no change in DNA content beyond the 3 week time point and linearly extrapolated the amount of MSC collagen production to 6-weeks.

We determined an approximate 12% increase in MSC collagen production was found at 6 weeks in the CFF-specimens over use of bFGF/AA2P alone, while dynamic conditioning at the organ-level produced an ~18% increase over dynamically conditioned CFF specimens. bFGF and AA2P supplemented media accelerated collagen formation during at 3 weeks (~185% increase in collagen mass/MSC compared to non-supplemented media), as well as increasing collagen mass production from 3.90 to 4.43 pg/cell/week from 3 to 6 weeks. Using supplemented media, TEVC physiologic conditioning increased collagen mass production rate from 7.23 to 13.65 pg/cell/week (88.8%) during the dynamic culture period, along with greater preservation of net DNA. Moreover, when compared to our previous CFF study under combined cyclic flexure and sub-physiological flow, physiologic conditioning increased collagen production rate from 4.76 to 6.42 pg/cell/week (35%).

CFD Analysis

CFD analysis was able to converge to solutions at the specified criterion (residual values≤$10^{-9}$). The CFD analysis were performed on fully bent CFF bioreactor specimens indicated that there was a strong oscillatory component associated with the flow field, particularly on the inner wall of the sample. The magnitude of shear stresses was higher on the outer wall of the specimens as compared to the inner wall. However, owing to the low inlet velocity prescribed for the CFD model (prescribed based on the experimental conditions of flow source velocity=2000 RPM reported previously), the shear stresses were in the subphysiologic range, consistent with the findings of a previous CFD study on the CFF bioreactor. As a means to quantify the magnitude of oscillatory shear that occurs, the following oscillatory shear index was used $$OSI = \frac{1}{2}\left(1 - \frac{\left|\int_0^T \tau_w \, dt\right|}{\left|\int_0^T |\tau_w| \, dt\right|}\right) \quad (2)$$

where $\tau_w$ is the wall shear stress, T is the period, and t is time. The OSI has a maximum value of 0.5 that represents pure oscillatory flow. Spatial variations in OSI were quantified between two landmark vortices over 11 instantaneous time points in a 0.5 Hz cycle from fully straight to increasingly bent CFF bioreactor specimen configurations. A large portion of the specimen inner wall experiences a high level of oscillatory shear.

Previous work has described the complex surface flow patterns that native tri-leaflet valves. As observed in the CFF specimens, flow reversal also occurs in the native leaflet, with oscillatory fluid-induced stress effects residing on the aortic side. Other dominant features of the flow field are the relative lower shear stresses on the aortic side of the valve compared to the ventricular side. The overall flow patterns and magnitude of fluid-induced surface shear stresses were similar between the inner wall of the CFF-bioreactor specimens and the aortic side of the leaflet. However, the commissure and basal attachment regions of the ventricular side of a native aortic valve experiences w62-82% higher shear stresses over the peak fluid-induced stresses that were experienced by the CFF specimens conditioned at sub-physiological flow conditions.

Discussion

There is general agreement that mechanical conditioning provides the necessary stimuli to promote proper tissue formation in engineered tissues. We have shown that mechanical stimulation augmented both collagen intrinsic stiffness and mass. This result demonstrated that basic approaches to promote tissue formation by physical stimulation have effects beyond just the upregulation of tissue component mass production. The mechanical quality, regulated by how the collagen is laid down (form and content), is also modified. Moreover, these results cannot be obtained by 2D tissue systems; full 3D approaches like that used herein are clearly required to determine how cellular stimulation translates into specific ECM formation.

Critical to the application to any TEHV approach is an understanding of the time evolution of the ECM stiffness and how it is modulated by physical conditioning. Although such approaches have been established for a range of tissues, particular challenges are encountered for heart valves, which exist in a highly dynamic, fluidic environment that induces very large tissue stresses. Moreover, these functional demands must be meet at the time of implantation—no stress shielding or other protective interventions are possible. For engineered heart valve tissues, the modeling of such approaches is still in its infancy. To achieve this task from a bio-mimetic standpoint, appropriate organ-level studies are required wherein the valves are compelled to cyclically open and close, and in doing so are subjected to the complex coupled flow, flexure and stretch stress states that native valves experience. Related studies concerning the potential of MSCs in heart valve tissue engineering, in this study, we seeded MSCs on tri-leaflet valve-shaped PGA/PLLA scaffolds. Subsequently, we investigated the effects of dynamic organ-level valve conditioning at physiological, pulmonary artery pressures on bulk engineered tissue formation, namely the collagen and GAG production. In addition, we conducted these studies by simultaneously attempting to improve tissue culture media conditions by supplementing it with bFGF/AA2P.

Collagen and GAGs have unique function in heart valves, and inclusion of these two components will be essential for the development of any engineered heart valve tissue, even if the specific distribution and architecture differs from native valves. We were able to demonstrate, prior to any mechanical conditioning, that media supplementation with bFGF/AA2P augments collagen production substantially at the initial (first 3 weeks) culture times. Further, it provides at a minimum a threshold amount of collagen that may likely contribute towards adequate stiffness characteristics of the construct.

The present TEVC studies demonstrated more robust collagen formation compared to our previous CFF studies (~35% increased rate of collagen production/cell). The DNA content of the TEPV constructs was maintained beyond the initial 3-week static culture period when dynamic conditioning was performed for a subsequent 3 weeks. These assay results demonstrate that either, a larger number of viable MSCs are retained and/or the ability of the cells to secrete more collagen increases with physiological pressure-based conditioning.

Consistent with previous studies performed in our laboratories, there was a reduction in GAG concentration (i.e. in proportion with the total tissue mass) with an increase in culture time. Flanagan et al. (A collagen-glycosaminoglycan co-culture model for heart valve tissue engineering applications. Biomaterials 2006; 27(10):2233-46) have shown that incorporation of a GAG component to the scaffold environment results in enhanced extracellular matrix production. Another study (Balguid A, et al. Hypoxia induces near-native mechanical properties in engineered heart valve tissue. Circulation 2009; 119(2):290-7) showed that GAG production approached near native valve levels in tissue engineered heart valves under hypoxic and insulin-rich environments. Further studies will be required to better understand the role of GAGs in TEPV development.

The Role of Oscillatory Flow Patterns on MSC ECM Production

Fully unidirectional forward flow when CFF specimens were straight reduced with increasing specimen flexure. At greater flexure states large regions of flow reversal were found and, in particular, complete flow reversal on the inner walls of the samples was observed. The large extent to which the flow is reversed during CFF specimen flexure points towards a high oscillatory component that is associated with the fluid-induced shear stresses that act on the surface of the specimens. We were able to confirm this by quantifying the purely oscillatory nature of the surface fluid flow (OSI=0.5) in regions of the inner wall. In order for scaffold deformations to induce significant tissue formation, sufficient cellular strains must occur for cellular transduction events to occur. However, that the nonwoven PGA-PLLA scaffolds used in this study undergo relatively modest strains under tension (unpublished observations) and thus experience small strains when TEVC is in the fully closed, loaded position. Further, in flexure they undergo an estimated at most ±7% tensile/compressive strain.

Taken as a whole, it is unlikely that scaffold straining alone can be sole underlying contributor to augmented tissue formation found to occur under combined flexure and flow conditions. This observation is further supported by the modest levels of tissue formation detected in the flexure-only experiments, which were also comparable in magnitude to the steady flow alone group. More importantly, in both the previous and current studies, only with time-varying movement (flex-flow or organ level conditioning) were the rates of collagen formation substantially increased over the flex and flow (wherein the flow fields were relatively static) conditions alone. Our current CFD results suggest that the only remaining extrinsic physical factor was the presence of time-varying surface shear stresses that occur with time-varying movement (flex-flow or organ level conditioning). We thus hypothesize that oscillatory surface shear stresses induced by the time-varying flow patterns induced by the deforming scaffolds or leaflets play a major role in stimulating engineered tissue formation in MSC-seeded scaffolds.

Support for this hypothesis exists in the bone tissue engineering literature, where oscillatory fluid flow preserves healthy osteogenic tissue, upregulates transcription factors involved in multiple differentiation pathways of MSCs, and has been found to increase MSC proliferation. While the specific molecular mechanisms involved in each of these pathways are still largely unknown, it has been recently shown that non-canonical Wnt and N-Cadherin related b-Catenin signaling are involved in the osteogenic pathway of MSCs. In addition, Arnsdorf et al (Mechanically induced osteogenic differentiation—the role of RhoA, ROCKII and cytoskeletal dynamics. J Cell Sci 2009; 122(Pt 4):546-53) demonstrated that oscillatory flow regulates multiple genes (runx2, sox9 and PPARg) in MSCs that can commit the cells to osteogenic, chondrogenic and adipogenic lineages. MSC signaling was induced by the direct effect of oscillatory fluid flow exerting a greater tensile load on the actin cytoskeleton. On the other hand, pure chemical inducement of actin tension alone was not sufficient to upregulate gene expression.

These findings suggest that unique, external mechanical conditioning regimes that have fluid-induced oscillatory shear stresses may play a critical role in engineered tissue development that utilize MSCs. Practically, such simulation regimes could be exploited to assist in engineered heart valve tissue formation using optimized bioreactor protocols. The extent to which these regimes impact MSC trans-differentiation and phenotype, as well as the underlying cell-cell signaling occurring within the engineered tissue, remains to be elucidated.

Limitations: The PGA-PLLA scaffolds utilized here were chosen on the basis of their well characterized mechanical behavior and extensive use in ours and other laboratories. However, PGA/PLLA scaffolds are not elastomeric, do not permit large deformations, and are not able to produce a TEVC that duplicated native valve motion. However, it is unlikely that these limitations qualitatively affected our results, but rather our findings represented a lower bound tissue formation likely to be found under fully simulated valve dynamics.

CONCLUSIONS

Overall, we found that when MSC-seeded TEVC are subjected to dynamic simulated organ level conditions they exhibited increased collagen mass production levels and rates compared to our earlier CFF study. Moreover, given the fact that the seeded scaffolds underwent at most modest strains during either CFF or physiological conditioning, the oscillatory surface shear stresses estimated in both studies suggest that they may play a significant role in eliciting MSC collagen production in the highly dynamic engineered heart valve fluid mechanical environment. This speculation is supported by quasi-static CFD simulations that indicated specific flow features, such as flow reversal previously reported in native valves, are replicated in a fully bent CFF bioreactor specimen. With respect to of native leaflets, flow vortices on the aortic side increase speed and efficiency of valve closure by impinging on the leaflet in the direction that favors coaptation, thereby assisting valve dynamics. From a tissue engineering viewpoint, oscillatory shear stresses may be exploited to enhance collagen production within the complex heart valve fluidic environment during the in-vitro tissue formation phase.

Whereas particular embodiments of this invention have been described above for purposes of illustration, it will be evident to those skilled in the art that numerous variations of the details of the present invention may be made without departing from the invention as defined in the appended claims.

We claim:
1. A tissue conditioning bioreactor module comprising:
 a) a module body comprising a cylindrical, folded passage having a diameter ranging from 10 mm to 20 mm, the passage having an inlet, an outlet, an upstream portion, a bend, and a downstream portion that widens at a junction to define a cassette compartment with a diameter greater than that of the bend and the upstream portion and further comprising one or more actuator passages extending from the cassette compartment to outside the module body; and b) a tissue cassette within the cassette compartment comprising a tube having an inside diameter that is the same as the diameter of the downstream portion, an outside diameter, a lumen and an outside surface, the tube being fluidly connected to the downstream portion of the passage and the outlet and defining a gap between the outer surface of the tube and the cassette compartment, the cassette further comprising one or more tissue anchor pairs extending through the lumen of the tube, where each pair comprises a movable anchor and a fixed anchor, where the moving anchor passes out of the tube through openings in the tube into the gap and are mechanically coupled to one or more actuators that extend through the actuator passages to outside the module, such that movement of the one or more actuators moves the movable anchor relative to the fixed anchor.

2. The module of claim 1, comprising an annular member slidably disposed in the gap about the tube and connected to the movable anchor and the one or more actuators such that movement of the one or more actuators slides the annular member along the tube thereby moving the movable anchor within the tube.

3. The module of claim 1, in which the module comprises no magnetic parts.

4. The module of claim 1, in which the module comprises a sterilizable MRI-compatible polymer composition.

5. The module of claim 4, in which the sterilizable, MRI-compatible polymer composition comprises a polyimide.

6. The module of claim 4, in which the sterilizable, MRI-compatible polymer composition comprises a polyetherimide.

7. The module of claim 4, in which the sterilizable, MRI-compatible polymer composition comprises a polyether ether ketone (PEEK) or a polyethylene.

8. The module of claim 1 in which the bend is approximately 180 degrees.

9. The module of claim 1, further comprising a bioscaffold attached to a pair of adapters for engaging the movable and fixed anchors.

10. The module of claim 1, wherein the anchors are pins extending across the lumen of the tube.

11. The module of claim 1, wherein the tissue cassette is removable from the module.

12. The module of claim 1, wherein the passage and inside diameter of the tube has a diameter ranging from 12-14 mm in diameter.

13. The module of claim 1, wherein the passage and inside diameter of the tube is approximately 13 mm in diameter.

14. A device for conditioning tissue comprising a base, one or more of the modules of claim 1 and a reciprocating motor mechanically coupled to the actuators of the one or more modules such that reciprocation of a bar by the motor moves the actuators which move the moving anchors within the tube in the module.

15. The device of claim 14, further comprising a media reservoir, a pump fluidly connected to the media reservoir and the inlet of the one or more modules and a pump controller for controlling pump speed and timing.

16. The device of claim 15, wherein the outlets of the one or more modules are fluidly connected to the media reservoir so that media passing from the reservoir to the module is returned to the media reservoir.

17. A method of conditioning a tissue sample comprising attaching the tissue sample to a pair of adaptors for engaging the movable and fixed anchors, mounting the bioscaffold or tissue sample into the module of claim 1, and passing media through the module at laminar flow rates.

18. The method of claim 17, wherein the media is passed through the module at a flow rate that produces a Reynolds number of less than 2,300.

19. The method of claim 17, wherein the media is passed through the module at a flow rate that produces a shear stress of between 5.0 and 24 dynes/cm$^2$.

20. The method of claim 17, wherein the tissue sample is an engineered heart valve leaflet material.

* * * * *